US009399057B2

(12) United States Patent
Boyen et al.

(10) Patent No.: US 9,399,057 B2
(45) Date of Patent: Jul. 26, 2016

(54) SALMONELLA VACCINE

(75) Inventors: Filip Boyen, Merelbeke (BE); Frank Pasmans, Merelbeke (BE); Freddy Haesebrouck, Merelbeke (BE)

(73) Assignee: Universiteit Gent, Gent (BE)

( * ) Notice: Subject to any disclaimer, the term of this patent is extended or adjusted under 35 U.S.C. 154(b) by 305 days.

(21) Appl. No.: 13/575,119

(22) PCT Filed: Jan. 26, 2011

(86) PCT No.: PCT/EP2011/051034
§ 371 (c)(1),
(2), (4) Date: Nov. 9, 2012

(87) PCT Pub. No.: WO2011/092185
PCT Pub. Date: Aug. 4, 2011

(65) Prior Publication Data
US 2013/0052230 A1    Feb. 28, 2013

(30) Foreign Application Priority Data

Jan. 28, 2010 (EP) .................................. 10151956

(51) Int. Cl.
*C12P 1/00*      (2006.01)
*C12N 1/00*      (2006.01)
(Continued)

(52) U.S. Cl.
CPC ......... *A61K 39/0275* (2013.01); *A61K 2039/52* (2013.01); *A61K 2039/521* (2013.01); *A61K 2039/522* (2013.01); *A61K 2039/552* (2013.01)

(58) Field of Classification Search
CPC .......... C12N 1/00; C12N 15/00; C12N 15/01; C12N 15/09; C12N 15/63; C12N 15/66; C12N 15/74; A61K 38/00; A61K 39/00; A61K 38/164; A61K 39/025; A61K 39/0275; A61K 48/00; A61K 2039/51; A61K 2039/52; A61K 2039/521; A61K 2039/522; A61K 2039/523; C07K 14/195; C07K 15/255; C07K 2319/30; C07K 2317/55; C07K 2317/56; C07K 2317/622
See application file for complete search history.

(56) References Cited

U.S. PATENT DOCUMENTS

| | | | |
|---|---|---|---|
| 2004/0253712 A1 * | 12/2004 | Ausubel et al. ............. | 435/252.3 |
| 2007/0141086 A1 * | 6/2007 | Ohara .................. | A61K 9/0019 424/248.1 |
| 2008/0220022 A1 * | 9/2008 | Le Gros ............. | A61K 39/0275 424/258.1 |

FOREIGN PATENT DOCUMENTS

WO    WO 9401562    * 1/1994 ............. A61K 39/02

OTHER PUBLICATIONS

Zenk et al. (J of Immunol. 2009. 183(4):25697-2707).*

(Continued)

*Primary Examiner* — Ja'na Hines
(74) *Attorney, Agent, or Firm* — Dinsmore & Shohl LLP

(57) ABSTRACT

The present invention relates to novel *Salmonella* mutants, to a process for producing same and to vaccines containing same, wherein said *Salmonella* mutants are characterized in that they elicit a humoral response that can be distinguished from the humoral response elicited by the wild type strains. It is accordingly an object of the present invention to provide the use of said *Salmonella* mutants as serological marker strains in the vaccination of animals, in particular mammals and birds, more in particular cattle, poultry and pigs. The serological marker vaccine is of special value in animal farming and provides a (long-lasting) immunization against a wide range of *Salmonella* strains. The novel mutants are non-reverting and can be used for the efficient immunization of mammals and birds.

16 Claims, 5 Drawing Sheets

(51) Int. Cl.
    *C12N 1/12*     (2006.01)
    *C12N 1/20*     (2006.01)
    *A61K 39/112*     (2006.01)
    *A61K 39/00*     (2006.01)

(56) References Cited

OTHER PUBLICATIONS

Zenk et al (J of Immunol. 2009 vol. 183(4):25697-2707).*
Nevola et al., (Infect & Immun. 1985. vol. 50(1):152-159.*
Nagy et al., (Infect & Immun. vol. 74(10):5914-5925).*
Gabor Nagy et al., "Down-Regulation of Key Virulence Factors Makes the *Salmonella enterica* Serovar Typhimurium rfaH Mutant a Promising Live-Attenuated Vaccine Candidate", Infection and Immunity, vol. 74, No. 10, pp. 5914-5925, Oct. 2006.
Gabor Nagy et al., ""Gently Rough": The Vaccine Potential of a *Salmonella enterica* Regulatory Lipopolysaccharide Mutant", Live *Salmonella* Vaccine Candidate, 2008:198, pp. 1699-1706, Dec. 1, 2008.
Renee M. Tsolis et al., "Contribution of *Salmonella typhimurium* Virulence Factors to Diarrheal Disease in Calves", Infection and Immunity, .vol. 67, No. 9, pp. 4879-4885, Sep. 1999.
Renee M. Tsolis et al., "Identification of Putative *Salmonella enterica* Serotype Typhimurium Host Range Factor with Homology to IpaH and YopM by Signature-Tagged Mutagenesis", Infection and Immunity, vol. 67, No. 12, pp. 6385-6393, Dec. 1999.
Martin Selke et al., "Immunization of Pigs to Prevent Disease in Humans: Construction and Protective Efficacy of a *Salmonella enterica* Serovar Typhimurium Live Negative-Marker Vaccine", Infection and Immunity, vol. 75, No. 5, pp. 2476-2483, May 2007.
European Application No. 10151956.9 Search Report dated Sep. 15, 2010.

* cited by examiner

SALMONELLA VACCINE

FIELD OF THE INVENTION

The present invention relates to novel *Salmonella* mutants, to a process for producing same and to vaccines containing same, wherein said *Salmonella* mutants are characterized in that they elicit a humoral response that can be distinguished from the humoral response elicited by the wild type strains. It is accordingly an object of the present invention to provide the use of said *Salmonella* mutants as serological marker strains in the vaccination of animals, in particular mammals and birds, more in particular poultry, pigs and cattle. The serological marker vaccine is of special value in animal farming and provides a (long-lasting) immunization against a wide range of *Salmonella* strains. The novel mutants are non-reverting, and can be used for the efficient immunization of mammals and birds.

BACKGROUND TO THE INVENTION

Salmonellae are Gram-negative, facultative anaerobic, motile, non-lactose fermenting rods belonging to the family Enterobacteriaceae. Salmonellae are usually transmitted to humans by the consumption of contaminated foods and cause salmonellosis.

Salmonellae have been isolated from many animal species including, birds, cattle, sheep, pigs, dogs, cats, horses, donkeys, seals and reptiles. Ninety-five percent or more of the *Salmonella* serovars (ser.) isolated from food producing animals belong to *Salmonella enterica* subspecies *enterica* (*S. enterica*), with *Salmonella* ser. *Typhimurium* (*S. Typhimurium*), *Salmonella* ser. *Choleraesuis* (*S. Choleraesuis*), *Salmonella* ser. *Derby* (*S. Derby*), *Salmonella* ser. *Infantis* (*S. Infantis*), *Salmonella* ser. *Bredeney* (*S. Bredeney*), *Salmonella* ser. *Rissen* (*S. Rissen*), and *Salmonella* ser. *Anatum* (*S. Anatum*), as the most common serovars in pigs.

*Salmonella* infections are a serious medical and veterinary problem world-wide and cause concern in the food industry. Control of salmonellosis is important to avoid potentially lethal human infections and considerable economic losses for the social security and animal husbandry industry.

For said reasons, *Salmonella* monitoring programs aiming to reduce pork-related salmonellosis in humans are imposed all over the world. In a substantial proportion of these monitoring programs, the amount of *Salmonella*-directed antibodies in the blood or meat juice of pigs is used as the sole tool to categorize pig farms as low-risk or high-risk farms regarding their *Salmonella* status. The status of high-risk farm with respect to *Salmonella* can have serious implications for the national and international economical position of the company.

There has been a long history of the use of live attenuated *Salmonella* vaccines as safe and effective vaccines for the prevention of salmonellosis in animals and humans. Indeed, the live attenuated oral typhoid vaccine, Ty21a (Vivotif), manufactured by the Swiss Serum Vaccine Institute, has proved to be a very successful vaccine for the prevention of typhoid fever and has been licensed in many countries including the US and Europe. Pig farmers and veterinarians are reluctant to use vaccination in the control of *Salmonella* in pigs since vaccination with current vaccines cannot be distinguished from *Salmonella* infections using the serology based monitoring programs.

It is therefore desirable to develop a vaccine that would induce a good immune response, and that is serologically distinguishable from animals infected with *Salmonella*.

SUMMARY OF THE INVENTION

This invention is based on the finding that the humoral response elicited by *Salmonella* strains having mutations in the rf genes encoding for the *Salmonella* LPS O-antigens, is serologically different from the humoral response elicited by the wild type strains. The humoral response elicited by the mutant strains is significantly less detectable or even completely undetectable using the commercially available LPS-based ELISA's. These strains can therefore be regarded as serological marker strains, which are particularly useful in the manufacture of a vaccine to reduce *Salmonella* colonization in animals.

It is accordingly a first objective of the present invention to provide the use of a *Salmonella enterica* mutant strain, having at least one genetic modification within the rf genes encoding for the *Salmonella* lipopolysaccharide (LPS) O-antigens or in rf genes encoding the oligosaccharide core of LPS of *Salmonella*, in the manufacture of a serological marker vaccine. As will be apparent to the skilled artisan, for use in the manufacture of a serological marker vaccine, said genetic modifications include both naturally occurring genetic modifications within said genes, as well as artificially introduced genetic modifications.

In said serological marker vaccine, the rf genes are typically selected from the rf genes encoding for any one of the Ra, Rb1, Rb2, Rb3, Rc, Rd1, Rd2 and Re LPS chemotypes. In particular the rf genes are selected from the rf genes encoding for any one of the Ra, Rb1, Rb2, Rb3, and Rc LPS chemotypes. In one embodiment the rf genes are selected from the group consisting of rfbA, rfbT, rfaL, rfaJ, rfaK, rfaI, rfaB, rfaG, rfaF and rfaC; in particular rfbA, rfaL, rfaJ, rfaI, rfaG, rfaF and rfaC; more in particular rfbA, rfaL, and rfaJ; even more particular rfaL and rfaJ; in an even further embodiment the rf gene is rfaJ.

With the objective to obtain *Salmonella* serological marker strains, the rf gene mutations as defined in herein, can be applied in wild type *Salmonella enterica* serovars, including naturally occurring attenuated *Salmonella enterica* vaccine strains, as well as in artificially attenuated *Salmonella enterica* vaccine strains. The latter typically comprise one, two, three or more (auxotrophic) mutations. It is accordingly an object of the present invention to provide said attenuated *Salmonella enterica* vaccine strains, further comprising at least one genetic modification within the rf genes encoding for the *Salmonella* lipopolysaccharide (LPS) O-antigens or in genes encoding for the core components (oligosaccharide core) of the LPS of *Salmonella*. In a particular embodiment the present invention provides the *Salmonella enterica* mutant strain, having at least one genetic modification within the rf genes encoding for the *Salmonella* lipopolysaccharide (LPS) O-antigens or in rf genes encoding for the core components of the LPS of *Salmonella*, and further comprising one, two, three or more (auxotrophic) mutations.

In a particular embodiment the mutations are (auxotrophic) mutations in genes selected from aroA, purA, dam, his, cya/crp, htrA, Lon, phoP/phoQ, guaBA, nuoG, rpoS, rpoE, surA, thyA, aceA and the like.

The *Salmonella enterica* mutant strain as defined and used herein, includes any serotype of the *enterica* subspecies, and is typically selected from the group consisting of *Salmonella* ser. *Typhimurium* (*S. Typhimurium*), *Salmonella* ser. *Choleraesuis* (*S. Choleraesuis*), *Salmonella* ser. *Derby* (*S. Derby*), Salmonella ser. Infantis (*S. Infantis*), Salmonella ser. Bredeney (*S. Bredeney*), Salmonella ser. Rissen (*S. Rissen*), Salmonella ser. Anatum (*S. Anatum*), Salmonella ser. Hadar (*S. Hadar*), Salmonella ser. Virchow (*S. Virchow*), and Salmonella ser. Enteritidis (*S. Enteritidis*).

In a particular embodiment said strain is selected from the group consisting of Salmonella ser. Typhimurium (*S. Typhimurium*), Salmonella ser. Choleraesuis (*S. Choleraesuis*), Salmonella ser. Derby (*S. Derby*), Salmonella ser. Infantis (*S. Infantis*), Salmonella ser. Bredeney (*S. Bredeney*), Salmonella ser. Rissen (*S. Rissen*), and Salmonella ser. Anatum (*S. Anatum*). In a more particular embodiment said strain is Salmonella ser. Typhimurium.

In a further aspect the present invention provides a composition or a vaccine, i.e. a serological marker vaccine, comprising a Salmonella strain of the present invention, optionally comprising a pharmaceutically acceptable carrier or diluent.

The composition or the vaccine of the present invention, typically comprises from about $10^7$ to about $10^{10}$ CFUs of said Salmonella strain in a single dosage unit.

A further embodiment provides the composition or vaccine of the present invention for use in the treatment or prevention of a Salmonella infection in a subject, including veterinary infections.

Another embodiment provides the use of a Salmonella mutant strain of the present invention or of the vaccines of the present invention, in the treatment or prevention, i.e. immunization of swine and/or pig against Salmonella infection.

It is also an object of the present invention to provide a method for treating or preventing a Salmonella infection, comprising administering a Salmonella mutant strain as provided herein or a composition or vaccine of the present invention, to a subject in need thereof.

DESCRIPTION OF THE INVENTION

Figure 1:
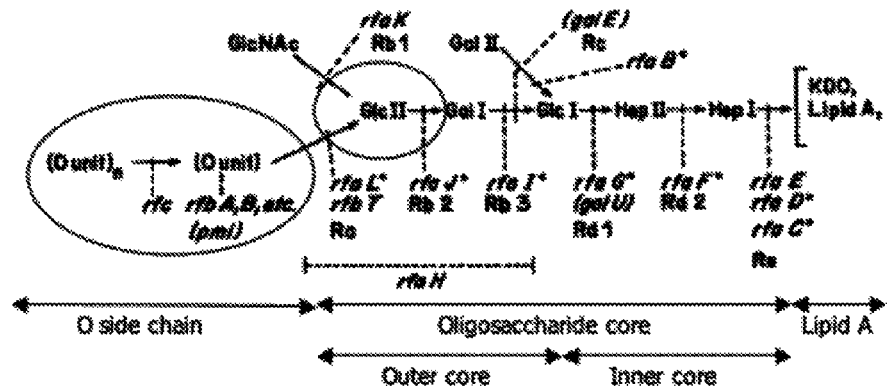
FIG. 1: Structure of *Salmonella Typhimurium* LPS, genes required for its synthesis and the corresponding chemotypes (Ra, Rb1, Rb2, Rb3, Rc, Rd1, Rd2, Re).
Figure 2:
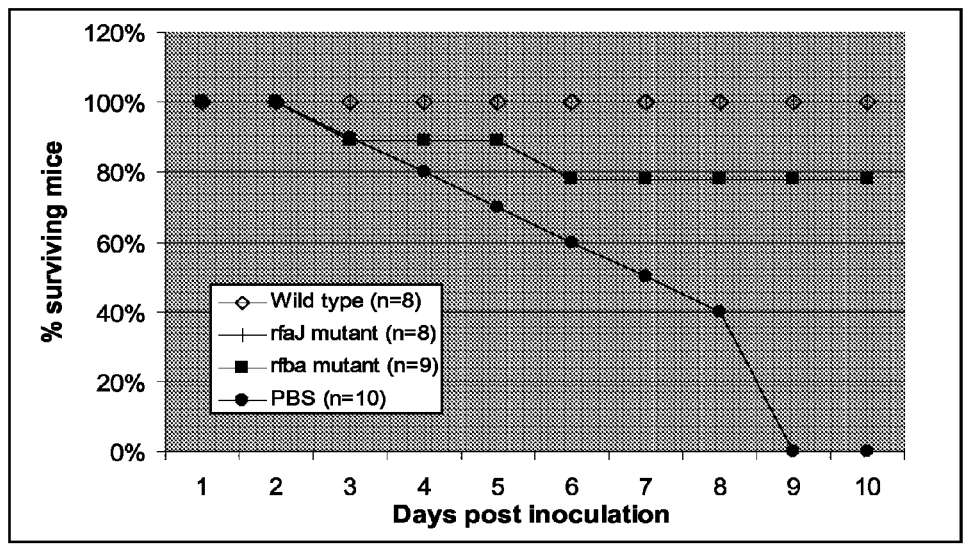
FIG. 2: Percentages of surviving mice at days one to 10 after inoculation. BALB\c mice were intragastrically vaccinated with either the wild type strain (+ control), the rfaJ mutant strain, the rfbA mutant strain and phosphate buffered saline (PBS; – control). Four weeks after vaccination, these mice were orally challenged with the highly virulent *Salmonella Typhimurium* strain NCTC 12023.
Figure 3:
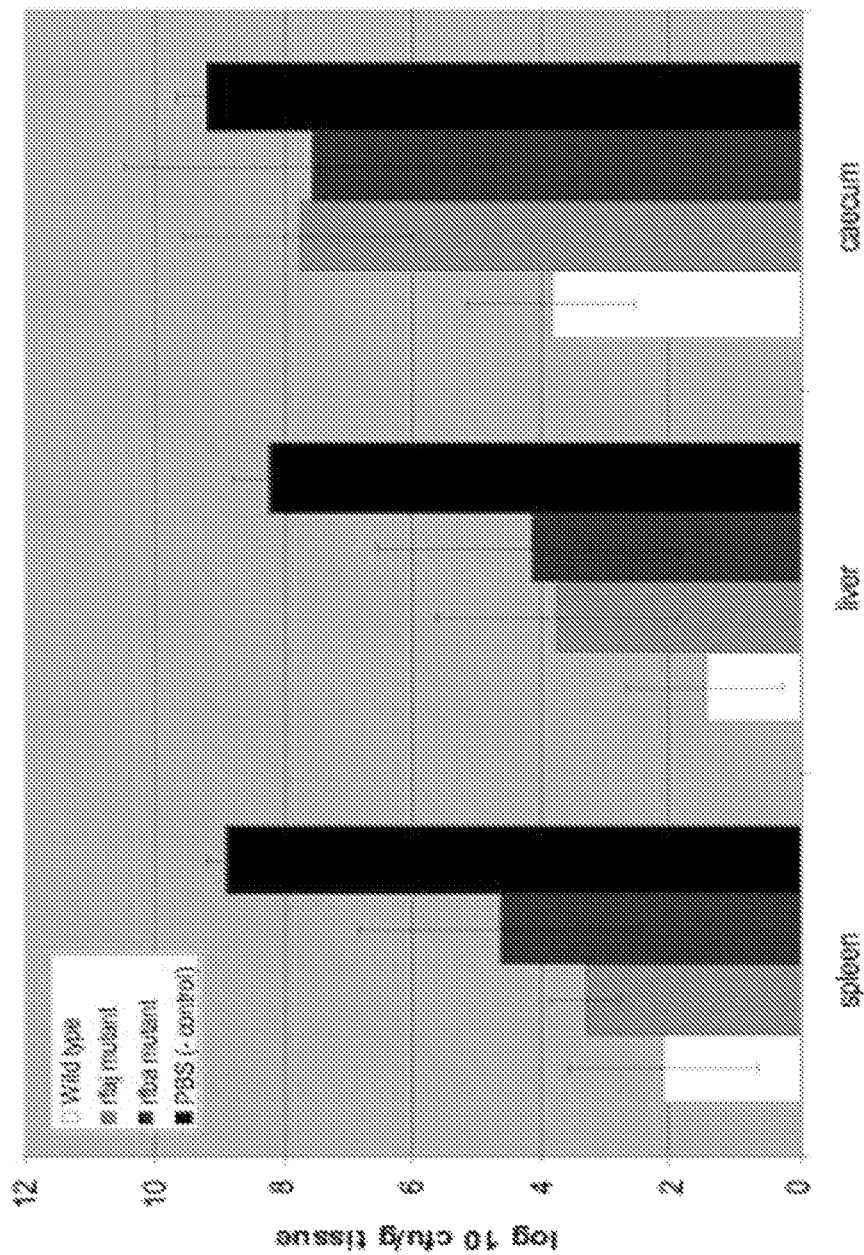
FIG. 3: Results of the quantitative bacteriological examination of the internal organs. BALB\c mice were intragastrically vaccinated with either the wild type strain (+ control), the rfaJ mutant strain, the rfbA mutant strain and phosphate buffered saline (PBS; – control). Four weeks after vaccination, these mice were orally challenged with the highly virulent *Salmonella Typhimurium* strain NCTC 12023. 10 Days after challenge, mice were killed and individual organs were isolated and analyzed for the presence of the challenge organisms.

The present invention provides mutant strains of *Salmonella enterica* that are useful as live, oral, attenuated or inactivated vaccines for inducing immunological protection against Salmonella, and characterized in that they elicit a humoral response that can be distinguished from the humoral response elicited by the wild type strains. The mutant strains of the present invention are characterized in that they contain at least one genetic modification within the rf genes encoding for the Salmonella lipopolysaccharide (LPS) O-antigens or in genes encoding the oligosaccharide core components of the LPS of Salmonella; i.e. within the genes encoding for the Ra, Rb1, Rb2, Rb3, Rc, Rd1, Rd2 and Re LPS chemotypes (see FIG. 1).

Lipopolysaccharide (LPS) is the major component of the outer membrane of Gram-negative bacteria, contributing to the structural integrity of the bacteria and as an endotoxin an important factor in the immune response elicited in vivo. LPS from members of the family of Enterobacteriaceae has been structurally analysed and as used herein consists of three well-defined regions. The first region, represented as the O-side chain in FIG. 1, also known as the O-specific antigen, the O-antigen or the somatic antigen; is a long-chain polysaccharide consisting of repeating units each containing one to seven monosaccharides. The second region, represented as the Oligosaccharide core in FIG. 1, also known as the LPS core, is composed of about seven monosaccharides (including heptose (Hep), glucose (Glc), galactose (Gal), and N'-acetylglucoseamine (GlcNAc)) and divided in the outer and the inner core region at the second side chain of the oligosaccharide core. The third region, represented in FIG. 1 as Lipid A, corresponds to the lipid anchor for the two outer regions, i.e. the O side chain and the oligosaccharide core, of the LPS molecule and consists of the eight-carbon keto sugar (KDO) that links the polysaccharide portions of the molecule to lipid A.

The strains lacking the LPS O-antigens and/or parts of the oligosaccharide core are phenotypically referred to as the R (rough) chemotypes (infra), and include the aforementioned Ra, Rb1, Rb2, Rb3, Rc, Rd1, Rd2 and Re LPS chemotypes. The genes encoding for said "rough" (genetically rf.) chemotypes are referred to as the rf genes, and include the aforementioned rfbA, rfbT, rfaL, rfaJ, rfaK, rfaI, rfaB, rfaG, rfaF and rfaC genes.

Deletion mutants, which completely lack the LPS O-antigen and oligosaccharide core, such as for example described in European Patent EP 0 158 282, result in the loss of the deeper inner core components (Rc, Rd and Re chemotypes). Since the loss of these deeper inner core components results in the instability of the *Salmonella* cell membrane and a substantial in vitro and in vivo attenuation, these deeper core deletion mutants are unsuitable for use as a vaccine strain (Nikaido, 1996). Compared to said deeper core deletion mutants, the mutant strains of the present invention have an incomplete LPS molecule lacking the O-antigens but still retaining the complete LPS core or parts thereof. Based on the remaining biochemical structure of the LPS core, said entities are annotated as chemotypes and represented by the entries in Roman type (Ra, Rb, etc. . . . ) in FIG. 1. It has now been found that the rf gene mutants of the present invention retain the capability of inducing immunological protection against *Salmonella*, but are characterized in that they elicit a humoral response that can be distinguished from the humoral response elicited by the wild type strains.

Where it is known that the *Salmonella* LPS O-antigen is an important virulence factor, with a direct impact on the multiplication and immunogenicity of the organisms, it has now been found that *Salmonella enterica* strains comprising genetic modifications in at least one of the rf genes, and in particular in the rfaJ and/or rfaL gene, yield LPS mutants that not only retain a virulence and immunogenicity comparable to the wild type strain but also provide a (long-lasting) immunization across a wide range of *Salmonella* serotypes. As such the *Salmonella* mutant strains of the present invention are particularly useful as serological marker vaccines to reduce *Salmonella* colonization in animals. Hence, the "serological marker vaccine" of the present invention is characterized in that it contains a *Salmonella* mutant strain whereby the deletion of one or more of the rf genes does not impair the production of *Salmonella*-specific antibodies and accordingly induce a good immune response that is serologically distinguishable from animals infected with wild-type *Salmonella* strains. Said vaccine is also referred to as a "DIVA vaccine" (differentiation between infected and vaccinated animals).

In a particular embodiment, the *Salmonella* mutant strains of the present invention are used as attenuated live vaccines. It is well established that live attenuated micro-organisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. In addition, unlike killed preparations, live vaccines are often more potent in inducing mucosal immune responses and cell-mediated responses, which may be connected with their ability to replicate in epithelial cells and antigen-presenting cells, such as macrophages, respectively.

The genetic modifications of the invention advantageously lead to a null-function, in other words impair or affect the gene function, and include both naturally occurring modifications, as well as artificially introduced modifications. The genetic modification may be an insertion, a deletion, and/or a substitution of one or more nucleotides in said genes. Deletion mutants are preferred. Although any serotype of *S. enterica* may be used, in preferred embodiments, the mutations are inserted into *S. enterica* serovars, such as for example *Salmonella* ser. *Typhimurium* (*S. Typhimurium*), *Salmonella* ser. *Choleraesuis* (*S. Choleraesuis*), *Salmonella* ser. *Derby* (*S. Derby*), *Salmonella* ser. *Infantis* (*S. Infantis*), *Salmonella* ser. *Bredeney* (*S. Bredeney*), *Salmonella* ser. *Rissen* (*S. Rissen*), and *Salmonella* ser. *Anatum* (*S. Anatum*). In a particular embodiment said mutation(s) are inserted a *Salmonella* ser. *Typhimurium* background.

It is also an object of the present invention to convert existing *Salmonella* vaccine strains, including naturally occurring attenuated *Salmonella enterica* vaccine strains, as well as artificially attenuated *Salmonella enterica* vaccine strains, into serological marker strains by introducing one or more of the rf gene mutations of the present invention into said existing vaccine strains.

Preferably, the mutants contain at least one genetic modification within one or more rf genes selected from the group consisting of rfbA, rfbT, rfaL, rfaJ, rfaK, rfaI, rfaB, rfaG, rfaF and rfaC; in particular rfbA, rfaL, rfaJ, rfaI, rfaG, rfaF and rfaC; more in particular rfbA, rfaL, and rfaJ; even more particular rfaL and rfaJ; in an even further embodiment the rf gene is rfaJ.

As used herein, the rf genes are meant to include any homolog or artificial sequence that is substantially identical, i.e. at least 70%, 75%, 80%, 85%, 87%, 89%, 90%, 92%, 93%, 94%, 95%, 96%, 97%, 98%, 99% or 100% identical to the corresponding rf genes as found in *Salmonella enterica* subsp. *enterica* serovar *Typhimurium* str. LT2 chromosome with NCBI reference sequence NC_003197.1.

In said sequence; –rfbA corresponds to CDS 2172670 . . . 2176548 having GeneID 1253616; –rfaL corresponds to CDS 3908290 . . . 3909504 having GeneID 1255237; –rfaJ corresponds to CDS 3912487 . . . 3913497 having GeneID 1255241; –rfaK corresponds to CDS 3909561 . . . 3910706 having GeneID 1255238; rfaI corresponds to CDS 3913515 . . . 3914528 having GeneID 1255242; rfaB corresponds to CDS 3914534 . . . 3915613 having GeneID 1255243; rfaG corresponds to CDS 3916738 . . . 3917862 having GeneID 1255246; rfaF corresponds to CDS 3906251 . . . 3907297 having GeneID 1255235; and rfaC corresponds to CDS 3907297 . . . 3908250 having GeneID 1255236.

Particularly the rf genes are meant to include any homolog or artificial sequence that is substantially identical, i.e. at least 70%, 75%, 80%, 85%, 87%, 89%, 90%, 92%, 93%, 94%, 95%, 96%, 97%, 98% or 99% identical to, more in particular consist of one or both of the rfaL and rfaJ genes as found in *Salmonella enterica* subsp. *enterica* serovar *Typhimurium* str. LT2 chromosome with NCBI reference sequence NC_003197.1, i.e. wherein rfaL (SEQ ID No. 2) corresponds to CDS 3908290 . . . 3909504 having GeneID 1255237 of NCBI reference sequence NC_003197.1; and rfaJ (SEQ ID No. 1) corresponds to CDS 3912487 . . . 3913497 having GeneID 1255241 of NCBI reference sequence NC_003197.1.

The percentage identity of nucleic acid and polypeptide sequences can be calculated using commercially available algorithms which compare a reference sequence with a query sequence. The following programs (provided by the National Center for Biotechnology Information) may be used to determine homologies/identities: BLAST, gapped BLAST, BLASTN and PSI BLAST, which may be used with default parameters. Hence, a particular embodiment of the present invention relates to a method to convert an existing *Salmonella* vaccine strain into a serological marker strain, said method comprising the following steps:

obtaining a *salmonella enterica* (vaccine) strain, and substituting or deleting part or all of the rfaJ or rfaL gene.

The method optionally further comprises one or more of the following steps:

creating a PCR adjusted antibiotic resistance cassette,
inserting a helper plasmid in the *Salmonella enterica* (vaccine) strain,
substituting part or all of the rfaJ or rfaL gene with the PCR adjusted antibiotic resistance cassette,
controlling the substitution with PCR and sequencing,
inserting the helper plasmid in the substituted target strain,
deleting the antibiotic resistance cassette and the helper plasmids, and
controlling the deletion with PCR and sequencing.

More specific, construction of deletion mutants in virulence genes according to the one-step inactivation method is e.g. described by Datsenko and Wanner (2000) optionally with some modifications (Donné et al., 2005).

In said embodiment wherein existing *Salmonella enterica* vaccine strains are converted into serological marker strains, the mutant strains according to the invention optionally include additional mutations (also referred to as auxotrophic mutations) introduced to improve for example the safety of the vaccine. Such additional mutations include, modifications in genes needed for the survival or the proliferation of the pathogen. Suitable genes for the auxotrophic mutation, include but are not limited to genes such as aroA, purA, dam, his, cya/crp, htrA, Lon, phoP/phoQ, guaBA, nuoG, rpoS, rpoE, surA, thyA, aceA and the like. Other genes that may be affected to improve the safety of the vaccine include virulence factors, such as for example SPI-1, SPI-2, SPI-3, Spi-4, Spi-5 and/or related effectors of flagellum, fimbriae, and adhesines; quorum sensing and/or biofilm associated genes; genes involved in stress response; genes involved with outer membrane proteins; and regulators of anyone of the aforementioned genes. Through the introduction of the genetic modification in the rf genes of the present invention, the existing vaccine strains will result in a different serological response of the animals to wild type strains and vaccine strains, and accordingly allows differentiating between vaccinated and infected animals using for example ELISA systems, more preferably LPS-based ELISA's.

When converting existing vaccines in serological marker vaccines, it is of utmost importance that the further modification does not affect the already weakened strain in its immunogenic and protective effect. It has now surprisingly been found that the rf gene mutations of the present invention have hardly any influence on the immunogenic and protective effect of existing *Salmonella* vaccines but allows to convert them into serological marker vaccines.

As already mentioned hereinbefore, the mutant *Salmonella* strains of the present invention may be used to manufacture a (pharmaceutical) composition or a vaccine composition, which may be administered to the subject via the parenteral, mucosal or oral route. Killed (inactivated) or live vaccines can be produced using art known procedures typically including a pharmaceutically acceptable carrier or diluent, and optionally an adjuvant.

For example, once the mutant strain is propagated to high colony forming units, it is inactivated by treatment with formalin, betapropriolactone (BPL), binary ethyleneimine (BEI), or other methods known to those skilled in the art. The inactivated strain is then mixed with a pharmaceutically acceptable carrier such as a saline solution, and optionally an adjuvant.

It is accordingly an object of the present invention to provide a pharmaceutical composition or a vaccine against e.g. salmonellosis comprising:

a life attenuated or an inactivated (killed) immunizing amount of a mutant strain according to the invention or of an immunogenic fragment thereof; and
a pharmaceutically acceptable carrier or diluent.

The term 'immunogenic' as used herein, i.e. in the phrase 'immunogenic fragments', refer to the capability of said strain fragments or molecules to elicit an immune response in an animal, in particular in a mammal, more in particular in a pig. The immune response may be humoral, cellular, or a combination of both.

The particular pharmaceutically acceptable carriers or diluents employed—are not critical to the present invention, and are conventional in the art. Examples of diluents include: buffer for buffering against gastric acid in the stomach, such as citrate buffer (pH 7.0) containing sucrose, bicarbonate buffer (pH 7.0) alone, or bicarbonate buffer (pH 7.0) containing ascorbic acid, lactose, and optionally aspartame. Examples of carriers include: proteins, e.g., as found in skimmed milk; sugars, e.g. sucrose; or polyvinylpyrrolidone.

The particular adjuvants employed are not critical to the present invention, and are conventional in the art. Examples of adjuvants include, but are not limited to, tensoactive compounds (such as Quil A), mineral salts (such as aluminium hydroxide), micro-organism derived adjuvants (such as muramyl dipeptide), oil-in-water and water-in-oil emulsions (such as Freund's incomplete adjuvant), particulate antigen delivery systems (such as liposomes, polymeric atmospheres, nanobeads, ISCOMs and ISCOMATRIX), polysaccharides (such as micro-particulate inulin), nucleic acid based adjuvants (such as CpG motivs), cytokines (such as interleukins and interferons), activators of Toll-like receptors and eurocine L3 en N3 adjuvantia.

By an "immunizing amount" as used herein means an amount that is able to induce a (protective) immune response in the animal that receives the pharmaceutical composition/vaccine. The immune response invoked may be a humoral, mucosal, local and/or a cellular immune response.

As is known to the skilled artisan, the immunizing amount or dose varies according to the route of administration. Those skilled in the art may find that the effective dose for a vaccine administered parenterally may be smaller than a similar vaccine which is administered via drinking water, and the like. The number of microorganisms that are required to be present in the formulations can be determined and optimised by the skilled person. However, in general, a patient may be administered approximately $10^7$-$10^{10}$ colony-forming units (CFUs), preferably approximately $10^4$-$10^9$ CFUs in a single dosage unit.

The mutant strains of the invention and pharmaceutical compositions or vaccines comprising same are highly suitable for immunizing animals against salmonellosis (i.e. an infection with *Salmonella* bacteria). Clinical signs of *Salmonella* infections in farm animals include, sudden death syndrome in feedlot cattle, *Salmonella* diarrhea, e.g. in baby calves and pigs, Pneumonia, stiffness, joint-ill and meningitis are also seen in *Salmonella* infections in farm animals. The mutant *Salmonella* strains of the invention, and pharmaceutical compositions or vaccines comprising same, are highly suitable for immunizing veterinary species, in particular cattle, poultry and swine, and even more in particular swine and piglets, against salmonellosis and possibly other diseases.

It is thus an object of the present invention to provide the use of mutant strains of *Salmonella enterica* of the present invention for preparing a medicament which is employed for the prophylactic and/or therapeutic treatment of *Salmonella* infection in animals, in particular in swine and piglets. In a preferred embodiment the present invention provides the use of the mutant strains of *Salmonella enterica* of the present invention, in the manufacture of a serological marker vaccine. The present invention thus also encompasses the mutant strains of *Salmonella enterica* as described herein for treating or preventing salmonellosis.

As already mentioned hereinbefore, the mutant microorganisms and vaccine compositions of the present invention may be prepared by known techniques.

The choice of particular *Salmonella enterica* microorganism, can be made by the skilled person without undue experimentation. A preferred microorganism is selected from the group consisting of *Salmonella* ser. *Typhimurium* (*S. Typhimurium*), *Salmonella* ser. *Choleraesuis* (*S. Choleraesuis*), *Salmonella* ser. *Derby* (*S. Derby*), *Salmonella* ser. *Infantis* (*S. Infantis*), *Salmonella* ser. *Bredeney* (*S. Bredeney*), *Salmonella* ser. *Rissen* (*S. Rissen*), *Salmonella* ser. *Anatum* (*S. Anatum*), *Salmonella* ser. *Hadar* (*S. Hadar*), *Salmonella* ser. *Virchow* (*S. Virchow*), and *Salmonella* ser. *Enteritidis* (*S. Enteritidis*).

In a particular embodiment said microorganism is selected from the group consisting of *Salmonella* ser. *Typhimurium* (*S. Typhimurium*), *Salmonella* ser. *Choleraesuis* (*S. Choleraesuis*), *Salmonella* ser. *Derby* (*S. Derby*), *Salmonella* ser. *Infantis* (*S. Infantis*), *Salmonella* ser. *Bredeney* (*S. Bredeney*), *Salmonella* ser. *Rissen* (*S. Rissen*), and *Salmonella* ser. *Anatum* (*S. Anatum*).

In one embodiment the microorganism is *Salmonella Typhimurium*; more in particular the *Salmonella Typhimurium* strain MB2486, also known as the *Salmonella Typhimurium* strain 112910a (Boyen F. et al., 2005; Boyen F. et al., 2006). The latter strain has been deposited on Mar. 5, 2010 with BCCM/LMG Bacteria Collection, Laboratorium voor Microbiologie—Universiteit Gent, K. L. Ledeganckstraat 35, B-9000 Gent, Belgium and has accession number LMG P-25625.

The genetic modifications or mutations may be introduced into the microorganism using any known technique. Preferably, the mutation is a deletion mutation, where disruption of the gene is caused by the excision of nucleic acids. Alternatively, mutations may be introduced by the insertion of nucleic acids or by point mutations. Methods for introducing the mutations into the specific regions will be apparent to the skilled person and are preferably created using the one step inactivation method described by Wanner and Datsenko (2000). Other methods can be applied to achieve a site directed mutagenesis (eg. using suicide plasmids), however the one-step inactivation method is generally accepted as the best and fastest way to achieve a knock-out deletion mutant.

As will be apparent from the examples hereinafter, it has been established by the present invention that strains lacking the O-side chain and parts of the LPS core, with in particular the Rb2 chemotype, can be regarded as serological marker strains, in that the deletion of the rf genes does not impair the production of *Salmonella*-specific antibodies and accordingly induce a good immune response that is serologically distinguishable from animals infected with wild-type *Salmonella* strains. The targeted LPS components (surrounded by a circle), their respective encoding genes and the general structure of LPS are depicted in FIG. 1.

In a particular embodiment of the present invention, the mutant strains are rfaJ and/or rfaL deletion mutants in *Salmonella Typhimurium* strain MB2486. This strain is a well-characterized porcine field strain that is able to cause persistent infections in pigs, both in field and experimental conditions. This strain does not harbour the virulence plasmid.

The contribution of virulence plasmids to the systemic phase of *Salmonella* infections is well described (Barth and Bauerfeind, 2005; Rychlik et al., 2006). At least six serotypes of *Salmonella* (serotypes *Abortusovis*, *Choleraesuis*, *Dublin*, *Enteritidis*, *Gallinarum/Pullorum*, and *Typhimurium*) are known to harbour a virulence plasmid. This does not mean that all isolates of these serotypes carry the virulence plasmid. Pigs generally carry more *Salmonella Typhimurium* strains lacking the virulence plasmid, compared to for example cattle or horses (Bauerfeind et al., 2001). The virulence plasmid has also been reported to be often absent from strains isolated from clinically healthy pigs or pigs showing only diarrhoea (Namimatsu et al., 2006). In contrast, the virulence plasmid was frequently observed in the isolates from systemically infected pigs (Namimatsu et al., 2006). It can therefore be assumed that strains lacking the virulence plasmid are still capable of colonizing the gut of pigs, but will less frequently lead to systemic infections, both in pigs, other animals and humans.

Implementation of monitoring programs and coordination of control measures are being used worldwide to prevent non-typhoidal *Salmonella* infections in humans from contaminated pork. Extensive national monitoring and control programs at the farm level are mostly conducted in the European countries (regulation [EC] 2160/2003, EFSA, 2006). The Danish, British, Irish and German programmes are based on serological testing of meat juice samples taken at the slaughterhouse, thus categorising the pig herds according to their assessed risk of carrying *Salmonella* into the slaughter plant. Belgian and Dutch monitoring programmes are similar, but the serological testing is currently performed on blood or serum samples collected on the farm. Farmers with herds belonging to the category with the highest risk of introducing *Salmonella* into the slaughterhouse are assisted by the national governments to reduce the *Salmonella* load of their herd (Boyen et al., 2008).

Vaccines using the described LPS serological marker strain deletions would thus not interfere with the existing *Salmonella* control programs that are based on serological testing, and applying the described LPS deletions in existing or newly developed *Salmonella enterica* vaccine strains would thus significantly increase the opportunities of using vaccination in the existing *Salmonella* control programs as a control measure. Thus vaccines comprising the mutant strains of the present invention have application to the prevention of *Salmonella* infections, in particular in swine and piglets.

To formulate the vaccine compositions, the mutant microorganisms may be present in a composition together with any suitable pharmaceutically acceptable adjuvant, diluent or excipient. Suitable formulations will be apparent to the skilled person. The formulations may be developed for any suitable means of administration. Preferred administration is via the oral, mucosal or parenteral routes and the vaccines are live attenuated *Salmonella* microorganisms.

The invention will be described in further details in the following examples and embodiments by reference to the enclosed drawings. Particular embodiments and examples are not in any way intended to limit the scope of the invention as claimed. The rationale of the examples given here for the serotype *S. Typhimurium* are equally well applicable to other *Salmonella enterica* serotypes infecting veterinary species, such as for example *Salmonella* ser. *Typhimurium* (*S. Typhimurium*), *Salmonella* ser. *Choleraesuis* (*S. Choleraesuis*), *Salmonella* ser. *Derby* (*S. Derby*), *Salmonella* ser. *Infantis* (*S.*

*Infantis*), *Salmonella* ser. *Bredeney* (*S. Bredeney*), *Salmonella* ser. *Rissen* (*S. Rissen*), and *Salmonella* ser. *Anatum* (*S. Anatum*).

The following Examples illustrate the invention

Example 1

Materials and Methods

All in vivo experiments were approved by the ethical committee of the Faculty of Veterinary Medicine, Ghent University (EC 2009/124, EC 2009/131, EC 2010/080, EC 2010/108, EC 2008/124 and EC 2009/57).

1. Bacterial Strains

*Salmonella Typhimurium* strain 112910a, phage type 120/ad, isolated from a pig stool sample and characterized previously (Boyen et al., 2009), and several isogenic LPS knock-out mutants (ΔrfbA, ΔrfaL, ΔrfaK, ΔrfaI, ΔrfaG, ΔrfaF), constructed in genes identified as maintenance and virulence genes, were used in this study. The knock-out mutants where constructed as described before (Boyen et al, 2006a) and are shown in table 2, primers used in this study are shown in table 3.

TABLE 2

Strains used in this study

| Strain | Genotype | Product of the deleted gene |
|---|---|---|
| WT Boyen et al. 2009 | *Salmonella Typhimurium* 112910a (O: 1, 4, 12) | No deletions |
| NCTC12023 Hensel et al. 1995 | *Salmonella Typhimurium* NCTC 12023 Nal$^r$ (O: 1, 4, 12) | No deletions |
| ΔrfaL | *Salmonella Typhimurium* 112910a ΔrfaL | *Salmonella Typhimurium* O-antigen ligase |
| Δrfaj | *Salmonella Typhimurium* 112910a ΔRfaj | LPS 1,2-glucosyltransferase |
| Δrfba | *Salmonella Typhimurium* 112910a ΔRfba | glucose-1-phosphate thymidylyltransferase |
| ΔrfaI | *Salmonella Typhimurium* 112910a ΔrfaI | LPS 1,3-galactosyltransferase |
| ΔrfaG | *Salmonella Typhimurium* 112910a ΔrfaG | LPS core biosynthesis protein |
| ΔrfaF | *Salmonella Typhimurium* 112910a ΔrfaF | LPS heptosyltransferase II |
| *Salmonella* Enteritidis | *Salmonella* Enteritidis Nal$^{20}$ (O: 1, 9, 12) | no deletions |
| *Salmonella* Heidelberg | *Salmonella* Heidelberg Nal$^{20}$ (O: 1, 4, 5, 12) | no deletions |
| WT Nal$^{20}$ Boyen et al. 2009 | *Salmonella Typhimurium* 112910a Nal$^{20}$ (O: 1, 4, 12) | no deletions |

TABLE 3

Primers used in this study to create the deletion mutants

| SEQ ID N° | Primers | Sequences |
|---|---|---|
| 3 | rfaJ forward | 5'- ATAGCCTACTTTAAACGTAAACTTCTTGAATAAAACCCATAGGTGATG TATGTGTAGGCTGGAGCTGCTTC- 3' |
| 4 | rfaJ reverse | 5'- AGTTTTTAATCTTTTTTTCAATAATCATAATGGAGATTTAGGGAGGGGAACATATGAATATCCTCCTTAG- 3' |
| 5 | rfbA forward | 5'- TAATAAATTTAAATGCCCATCAGGGCATTTTCTATGAATGAGAAATGGAATGTGTAGGCTGGAGCTGCTTC- 3' |
| 6 | rfbA reverse | 5'- GGCTCTAAGATCAAGACATCTGGTATTGCTGTTTTAATCACAATCATCACCATATGAATATCCTCCTTAG- 3' |
| 7 | rfaL forward | 5'- ATTAAAGAGACTCTGTCTCATCCCAAACCTATTGTGGAGAAAAGTGTGTAGGCTGGAGCTGCTTC- 3' |
| 8 | rfaL reverse | 5'- TTGAGTCCTGATGATGGAAAACGCGCTGATACCGTCATATGAATATCCTCCTTAG- 3' |
| 9 | rfaI forward | 5'- TTTAAAAATTTTAATAATGCAATATTCTCGAAATTACAAAAGTGATCACTTGTGTAGGCTGGAGCTGCTTC- 3' |
| 10 | rfaI reverse | 5'- TTCAGCTATTTCTATCTCAGGAAATGAATCCATTACATCACCTATGGGTTCATATGAATATCCTCCTTAG- 3' |

TABLE 3-continued

Primers used in this study to create the deletion mutants

| SEQ ID N° | Primers | Sequences |
|---|---|---|
| 11 | rfaG forward | 5'-GAAAAAATGCTGCCGCATGAGGCACGCACCATAGATTTGGACAGCCTGCTTGTGTAGGCTGGAGCTGCTTC- 3' |
| 12 | rfaG reverse | 5'-CCTCAAAAGCATCTTTACCGCGCCATAGTGTGGTTAACGGCGCTTTCAGCCATATGAATATCCTCCTTAG- 3' |
| 13 | rfaF forward | 5'-GCCGAAGGCGTCACGGAGTATATGGCCTGGCTGAACCGCGACGCGTAAGTTGTGTAGGCTGGAGCTGCTTC- 3' |
| 14 | rfaF Reverse | 5'-GGTATGTAATACGTCGCCCATCGATGATGTTTTAACGATCAAAACCCGCACATATGAATATCCTCCTTAG- 3' |
| 15 | rfaC Forward | 5'-CAGCGGGTTCTGGAAGAGCTTCATTCGCTGTTGTCGGAAGAGGGCGTTTATGTGTAGGCTGGAGCTGCTTC- 3' |
| 16 | rfaC Reverse | 5'-GTGGTTAGCATCTTTTCTCCACAATAGGTTTGGGATGAGACAGAGTCTCTCATATGAATATCCTCCTTAG- 3' |

Briefly, the genes of interest were first substituted by a PCR adjusted antibiotic resistance cassette (kanamycin) using the helper plasmid pKD46. This plasmid encodes the phage λ Red system, which promotes recombination between the native gene and the PCR adjusted antibiotic resistance cassette. Recombinant clones were selected by plating on Luria-Bertani agar (LB; Sigma Aldrich Chemie Gmbh, Steinheim, Germany) containing 100 µg/ml kanamycin. The substitution was confirmed by PCR. In the last step, the antibiotic resistance cassettes were eliminated using the helper plasmid pCP20. The targeted genes were completely deleted from the start codon through the stop codon, as confirmed by sequencing.

Salmonella challenge strains comprised, spontaneous mutants resistant to 20 µg/ml nalidixic acid (Nal$^{20}$) in a NCTC12023 Salmonella Typhimurium strain highly virulent in BALB/c mice, in a Salmonella Enteritidis strain SE147, in a Salmonella Heidelberg strain 704Sa06 and in a Salmonella Typhimurium strain 112910a. All bacteria were routinely grown in LB broth or on brilliant green agar (BGA) at 37° C., unless stated otherwise.

A nalidixic acid-resistant Salmonella Typhimurium strain (NCTC 12023) was used in the second in vivo experiment for challenge of mice and this to minimize irrelevant bacterial growth when plating spleen, liver and caecum samples. This strain has the same serotype as the Salmonella Typhimurium strain 112910a used to make the knock-out mutants, but differ from the latter in its virulence in mice. Compared to the Salmonella Typhimurium strain NCTC 12023, the Salmonella Typhimurium strain 112910a lacks the virulence plasmid that is known to have an important contribution to the systemic phase of Salmonella infections in animals (Barth and Bauerfeind, 2005; Rychlik et al. 2006).

2. Characterization of the LPS Knock-Out Mutants of Salmonella Typhimurium

Validation of the LPS phenotype occurred by SDS-polyacrylamide gel electrophoresis and fluorescent staining. For this purpose LPS was isolated from Salmonella Typhimurium strain 112910a and its isogenic knock-out mutants using a commercially available LPS extraction kit (Intron biotechnology, Gyeonggi-do, Korea). The obtained LPS was quantified using a ToxinSensor™ Chromogenic LAL Endotoxin Assay Kit (GenScript, Piscataway, USA) and was separated by standard SDS-polyacrylamide gel electrophoresis. LPS was stained using a Molecular probes Pro-Q Emerald LPS Gel stain kit (Invitrogen, Oregon, USA), creating a bright green-fluorescent signal, which was visualised with a 300 nm UV-transilluminator. To verify whether LPS mutant strains (ΔrfbA, ΔrfaL, ΔrfaJ, ΔrfaI, ΔrfaG, ΔrfaF) were still expressing O-antigens on their surface, an in vitro agglutination test (PRO-LAB $O_4$ and $O_{12}$ antisera, diagnostics, Austin, Tex.) was performed, according to the manufacturer's instructions. The smooth phenotype was also tested by checking sensitivity of Salmonella Typhimurium and its isogenic knock-out mutants to bacteriophage P22 as described elsewhere (Boyen et al., 2006a). As a measure of in vitro virulence of the wild type strain and its isogenic mutants, invasiveness of all strains was assessed in porcine epithelial cells (IPEC-J2) using a gentamicin protection assay as described previously (Boyen et al., 2006b).

3. ELISA Procedures

A commercially available enzyme-linked immunosorbent assay (ELISA) (HerdChek Salmonella; IDEXX Laboratories, Schiphol-Rijk, Noord-Holland, The Netherlands) for the detection of porcine antibodies against the LPS of Salmonella was used as a reference according to the manufacturer's instructions. Coating antigens in this ELISA include LPS of serogroups B, C1 and D (O-antigens 1, 4, 5, 6, 7 and 12) (Farzan et al., 2007). Besides, an in-house Salmonella Typhimurium strain 112910a whole cell ELISA, to detect porcine anti Salmonella Typhimurium antibodies, was prepared as follows. Salmonella Typhimurium strain 112910a was cultured overnight at 37° C. in 500 ml LB broth. Inactivation was achieved by adding 0.18% (v/v) formalin overnight at 37° C. The bacteria were centrifuged three times (5000×g for 30 min at room temperature) and the resulting pellet was resuspended in a volume of 250 ml Phosphate Buffered Saline (PBS) with 0.18% formalin and incubated overnight at 37° C. The inactivated culture was centrifuged again (5000×g for 10 min at 5° C.) and the pellet was resuspended in a final volume of 250 ml coating buffer (1.08 g $Na_2CO_3.10H_2O$, 0.968 g $NaHCO_3$, 0.25 l aqua ad iniectabilia 100% w/v). F96 maxisorp Nunc-immuno plates (Nunc; Denmark) were coated with 140 µl formalin-inactivated *Salmonella* strains diluted in coating buffer to an optical density of 660 nm, measured using a spectrophotometer (Ultraspec III®), incubated for 24 h at 4° C. and washed three times with 100 µl wash buffer (0.6 g $NaH_2PO_4.2H_2O$, 5.6 g $NaH_2PO_4.12H_2O$, 0.5 ml Tween 20 (Merck, Germany), 12.5 g NaCl). Plates were stored at 4° C. until used. Before starting the assay, the plates were washed with 100 µl destillated water (AD)+1% milk powder to prevent non-specific binding. A 1/2000 dilution of sera (100 µl) was added to the wells. The cut-off optical density was calculated as the mean obtained from the sera from a bacteriologically and serologically *Salmonella* free pig (the negative control, determined using the HerdChek ELISA) plus two times the standard deviation. All measurements were performed in triplicate.

4. Vaccine Preparation

For preparation of the inactivated vaccines, strains were cultured for 9 h at 37° C. in 400 ml LB broth and were concentrated to $10^9$ colony forming units per ml (cfu/ml) (in vivo trail 1) or 4.10 cfu/ml (in vivo trail 2). Inactivation was achieved by adding 2 ml 36% formalin (VWR international; Fontenay sous bois, France) overnight at 37° C. The formalin-inactivated *Salmonella* strains (FISS) were centrifuged twice (5000×g for 30 min at room temperature) and the resulting pellet was resuspended in 11 ml phosphate-buffered saline (PBS) with 55 µl 36% formalin and incubated overnight. Finally, 187 µl sterilized Tween 80 (Sigma Aldrich Chemie Gmbh, Steinheim, Germany) and 352 µl mannide monooleate (Sigma Aldrich Chemie Gmbh, Steinheim, Germany) was added and marcol oil (Esso Belgium nv, Antwerp, Belgium) was added to a final volume of 22 ml. To check inactivation, all vaccines were cultured on Columbia agar plates containing 5% sheep blood (COL; Oxoid, Wesel, Deutschland) and incubated aerobically and anaerobically overnight at 37° C.

Live attenuated vaccines were prepared as follows. Strains were grown overnight on a shaker at 37° C. in 100 ml LB broth. The bacteria were washed twice in PBS and centrifuged at 3500×g for 15 min at room temperature and diluted in PBS to the appropriate concentration of $10^8$ cfu/ml. The number of viable bacteria was determined by plating tenfold dilutions on Brilliant green Agar (BGA; Oxoid, Basingstoke, UK).

5. In Vivo Trail 1: Immunization of Piglets 5.1. Fifteen 6-week-old, bacteriological and serological *Salmonella* negative, piglets (commercial closed line based on Landrace) arrived at the faculty and were housed together at 25° C. under natural day-night rhythm with ad libitum access to feed and water. The piglets were randomly allocated to four vaccinated groups and one sham-vaccinated control group, each group consisting of three animals. One and three weeks after their arrival, pigs were intramuscularly vaccinated with 1 ml $5×10^8$ of one of the FISS (either WT, Δrfaj, or Δrfba). The control group was injected with 1 ml of sterile PBS.

Four weeks after arrival the pigs were humanely euthanized and blood samples were taken from the vena jugularis externa, using a Venoject system (Terumo; Roma, Italia). To determine the titers of anti-*Salmonella* lipopolysaccharide (LPS) antibodies, two commercially available enzyme-linked immunosorbent assay (ELISA) kits were used: the HerdChek *Salmonella* ELISA (IDEXX Laboratories, Schiphol-Rijk, Noord-Holland, The Netherlands) and the Salmotype Pig Screen ELISA (Labor Diagnostik Leipzig, Leipzig, Germany). Coating antigens in these ELISA's include LPS of serogroup B, C1 and D (O-antigens 1, 4, 5, 6, 7 and 12). The commercial available LPS based ELISA kits were carried out according to the manufacturer's instructions.

All sera samples were also examined using an in-house *Salmonella Typhimurium* strain 112910a whole cell ELISA, prepared as described before.

Before starting the assay, the plates were washed with 100 µl AD+1% milk powder to prevent non-specific binding. Serum proved to be *Salmonella* positive and serum proved to be *Salmonella* negative, were used as a positive and a negative control. A 1/2000 dilution of the sera (100 µl) was added to the wells. The cut-off OD was calculated as the mean obtained from the sera from the *Salmonella* free pig (the negative control) plus two times the standard deviation. Results are shown in table 1.

5.2. In a further study, we examined whether it was possible to discriminate between the serological response induced after immunization of pigs with the wild type and its isogenic ΔrfaL and ΔrfaJ strains. For this purpose, we immunized pigs with adjuvanted bacterins of either the wild type strain, the ΔrfaL strain or the ΔrfaJ strain to maximize antibody production (Nichols et al., 2010). Fourteen, 6-week-old, bacteriologically and serologically *Salmonella* negative piglets (commercial closed line based on Landrace) were housed together at 25° C. under natural day-night rhythm with ad libitum access to feed and water.

For preparation of antigen suspensions for immunization of pigs, strains were cultured for 9 hours at 37° C. in 400 ml LB broth and were adjusted to $5×10^8$ CFU/ml. Inactivation was achieved by adding 0.18% (v/v) formalin (VWR international, Fontenay sous bois, France) overnight at 37° C. The formalin-inactivated *Salmonella* strains were washed twice (5000×g for 30 min at room temperature) and the resulting pellet was resuspended in 11 ml PBS with 0.18% formalin and incubated overnight. Thereafter, this suspension was mixed with 11 ml marcol oil (Esso Belgium nv, Antwerp, Belgium) containing 3.4% sterilized Tween 80 (Sigma Aldrich Chemie Gmbh, Steinheim, Germany) and 6.4% mannide monooleate (Sigma Aldrich Chemie Gmbh, Steinheim, Germany). To check sterility, all suspensions were cultured on Columbia agar plates containing 5% sheep blood (COL; Oxoid, Wesel, Germany) and incubated aerobically and anaerobically overnight at 37° C.

Piglets were randomly allocated to three vaccinated groups (n=4) and one sham-vaccinated control group (n=2). One and three weeks after their arrival, pigs were intramuscularly immunized with one of the formalin-inactivated *Salmonella* strains (either: *Salmonella Typhimurium* strain 112910a, ΔrfaJ or ΔrfaL) with Freund's incomplete adjuvant to elicit an optimal humoral (antibody-mediated/Th2) response (Nichols et al., 2010). The control group was injected with 1 ml of sterile PBS. Four weeks after the second immunization, the pigs were humanely euthanized and blood samples were taken from the vena jugularis externa, using a Venoject system (Terumo; Roma, Italia). All sera samples were examined for the presence of anti *Salmonella Typhimurium* antibodies using the Herdchek ELISA and the in-house *Salmonella Typhimurium* strain 112910a whole cell ELISA, prepared as described previously.

6. Experimental Infection of Piglets with *Salmonella Typhimurium*

To obtain sera from *Salmonella Typhimurium* infected piglets, an experimental infection was performed with 4 week-old bacteriologically and serologically *Salmonella* negative piglets (commercial closed line based on Landrace). Piglets were randomly allocated in one experimental group (n=3) and one negative control group (n=3) and both groups were housed in separate isolation units at 25° C. under natural day-night rhythm with ad libitum access to feed and water. One week after their arrival at the facility, three experimental animals were orally inoculated with approximately $2 \times 10^7$ CFU/ml of a stationary phase culture of *Salmonella Typhimurium* strain 112910aNal[20] in 2 ml Hank's buffered salt solution (HBSS; Gibco Life Technologies, Paisley, Scotland); the negative control group (n=3) was sham-inoculated with 2 ml HBSS. The clinical condition of the pigs was monitored daily. Six weeks after oral inoculation, pigs were humanely euthanized and blood samples were taken from the vena jugularis externa, using a Venoject system (Terumo; Roma, Italia). All sera samples were examined for the presence of anti *Salmonella Typhimurium* antibodies using the Herdchek ELISA and the in-house *Salmonella Typhimurium* strain 112910a whole cell ELISA, prepared as described previously.

7. In Vivo Trial 2: Immunization and Challenge of Mice

The protective capacity of the LPS deletion mutants was compared to that of the wild type strain using a mouse model.

7.1. Hundred twenty 5-week-old specified pathogen-free (SPF) BALB/c mice (Bio services, Janvier, France) were used in this study. Twelve groups of 10 mice were housed in special filter-topped cages at 25° C. under natural day-night rhythm with ad libitum access to food and water and enriched with mouse houses and play tunnels.

One day after arrival sixty mice were immunized via the orogastric route with 200 μl $1 \times 10^8$ cfu/ml of a live attenuated mutant strain (either ΔrfaJ, or Δrfba) or with the *Salmonella Typhimurium* field strain. The control group was sham-inoculated with 200 μl of sterile PBS.

One day and two weeks after arrival, the remaining sixty mice were subcutaneously vaccinated with 100 μl $2 \times 10^8$ cfu/ml of an inactivated mutant strain (either ΔrfaJ, or Δrfba) or with the *Salmonella Typhimurium* inactivated field strain. The control group was injected with 100 μl of sterile PBS.

Four weeks after arrival both vaccinated and unvaccinated mice were challenged with a total of $10^7$ cfu/ml of NCTC 12023 by the orogastric route. Following challenge of the animals clinical scores were given to each animal. Clinical signs were graded into five levels with 0=no symptoms; 1=slight symptoms; 2=medium symptoms; 3=moderate symptoms; 4=severe symptoms; 5=dead. Mice that reached humane endpoints were euthanized. Ten days postinfection, tissue samples (spleen, liver and caecum) were examined.

7.2. Five-week-old specified pathogen-free (SPF) BALB/c mice (Bio services, Janvier, France) were housed in filter-topped cages at 25° C. under natural day-night rhythm with ad libitum acces to feed and water and enriched with mouse houses and play tunnels. Bacterial inocula used for oral protection assays were prepared as follows. Strains were grown overnight on a shaker at 37° C. in 100 ml LB broth. The bacteria were washed twice in PBS at 3500×g for 15 min at room temperature and adjusted in PBS to the appropriate concentration of $2 \times 10^7$ colony forming units per ml (CFU/ml). The number of viable bacteria was determined by plating tenfold dilutions on BGA.

In a first experiment, we tested whether the LPS mutants affect the protective capacity of *Salmonella Typhimurium* strain 112910a against a subsequent challenge with a highly virulent strain. For that purpose seven groups of ten mice were inoculated first via the orogastric route with $2 \times 10^7$ CFU/ml of one of the LPS mutant strains (either ΔrfbA, ΔrfaL, ΔrfaJ, ΔrfaI, ΔrfaG or ΔrfaF) or with the wild type *Salmonella Typhimurium* strain 112910a. A control group of ten mice was sham-inoculated with sterile PBS. Four weeks after primary inoculation, all mice were challenged with a total of $10^8$ CFU/ml of the virulent *Salmonella Typhimurium* strain NCTC12023Nal[20] by the orogastric route.

In a second experiment, we tested whether truncation of the LPS chain in the ΔrfaJ strain promotes cross-immunity against other *Salmonella* serovars. Sixty mice were orally inoculated first with $2 \times 10^7$ CFU/ml of either the ΔrfaJ strain (n=20) or *Salmonella Typhimurium* strain 112910a (n=20). A control group of 20 mice was sham-inoculated with sterile PBS (n=20). Sixteen days after primary inoculation, ten mice of each group were challenged with a total of $10^8$ CFU/ml of either *Salmonella Heidelberg* strain 704Sa06 Nal[20] (n=10) or *Salmonella Enteritidis* strain SE147 Nal[20] (n=10).

In both in vivo experiments, mice were euthanized nine days post challenge.

7.3. Tissue samples (spleen, liver and caecum) were examined quantitatively for the presence of the respective *Salmonella* strain. Samples were weighed and 10% (w/v) suspensions were made in buffered peptone water (BPW; Oxoid, Basingstoke, UK) after which the material was homogenized with a stomacher. The homogenized samples were examined for the presence of *Salmonella* by plating 10-fold dilutions on BGA supplemented with nalidixic acid (BGA$^{NAL}$) If negative at direct plating, the samples were pre-enriched overnight in BPW at 37° C., enriched overnight at 37° C. in tetrathionate broth and then plated on BGA$^{NAL}$. Samples that were negative after direct plating but positive after enrichment were presumed to contain 60 CFU per gram tissue (detection limit for direct plating). Samples that remained negative after enrichment were presumed to contain 0 CFU per gram tissue.

8. Statistical Analysis

In all experiments, statistical analysis was performed using a one-way ANOVA test (in case of homogeneity of variances), with posthoc Bonferroni corrections or a nonparametric Mann-Whitney-U-test (in case of non-homogeneity of variances), using the SPSS Statistics 17.0 software (SPSS Inc., Chicago, USA). ELISA results were analysed by a one-way ANOVA and Bonferroni corrections were applied. A P-value of <0.05 was considered significant.

Results

1. Characterization of the LPS Knock-Out Mutants of *Salmonella Typhimurium*

A systematic truncation of the LPS chain occurred as a result of defects in genes coding for glycosyl or phosphoryl transferases (or epimerases) and is shown in FIG. 1. LPS patterns obtained by standard SDS-polyacrylamide gel electrophoresis of *Salmonella Typhimurium* strain 112910a, the O-antigen mutant (ΔrfbA), the outer core mutants (ΔrfaL, ΔrfaJ, ΔrfaI) and the inner core mutants (ΔrfaG, ΔrfaF) show a visible loss of O-antigens for core mutants (ΔrfaL, ΔrfaJ, ΔrfaI, rfaG, ΔrfaF) compared to *Salmonella Typhimurium* strain 112910a (results not shown). Loss of the rfbA gene resulted in the presence of a complete core without covalently bound O-antigen ("semirough" LPS), because the rfb locus is responsible for the biosynthesis of O-antigen (Hitchcock et al., 1986). The complete lack of O-antigens in core mutants was also confirmed by resistance to bacteriophage P22 and appearance of the "rough" phenotype. *Salmonella Typhimurium* strain 112910a showed the "wild-type" LPS structure and is denoted as "smooth" LPS (Hitchcock et al., 1986).

A slide agglutination test was used to verify expression of O-antigens on the surface of *Salmonella Typhimurium* 112910a and its isogenic knock-out mutants. While *Salmonella Typhimurium* strain 112910a showed a distinct agglutination within 60 seconds, little granular clumping was seen with the rfbA mutant strain. No agglutination was observed with ΔrfaL, ΔrfaJ, ΔrfaI, ΔrfaG and ΔrfaF strains, which confirmed a total loss of $O_4$ and $O_{12}$ antigens.

Figure 4:
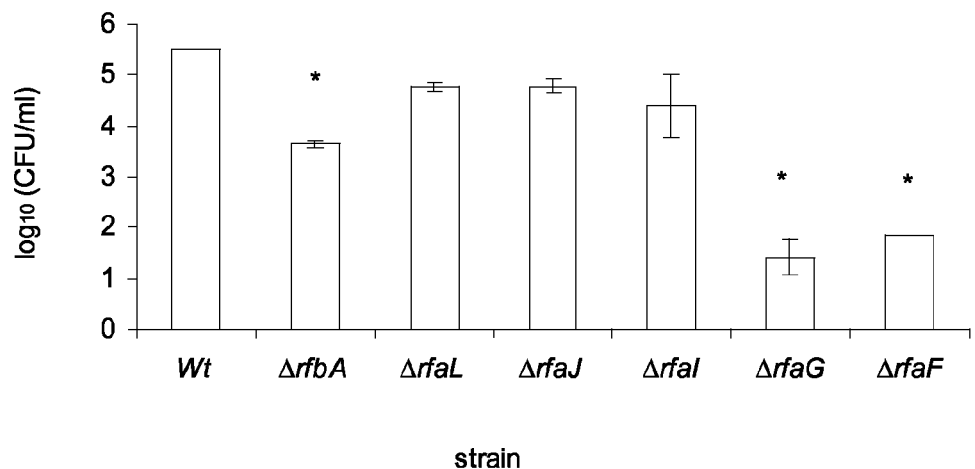
FIG. 4: The invasiveness of *Salmonella Typhimurium* and its isogenic knock-out mutants in IPEC-J2 cells. The log values of the number of gentamicin protected bacteria are shown. The results represent the means of three independent experiments conducted in triplicate and standard deviations are given. An asterisk refers to a significantly lower invasion compared to the wild type strain (P<0.05).
Figure 5:
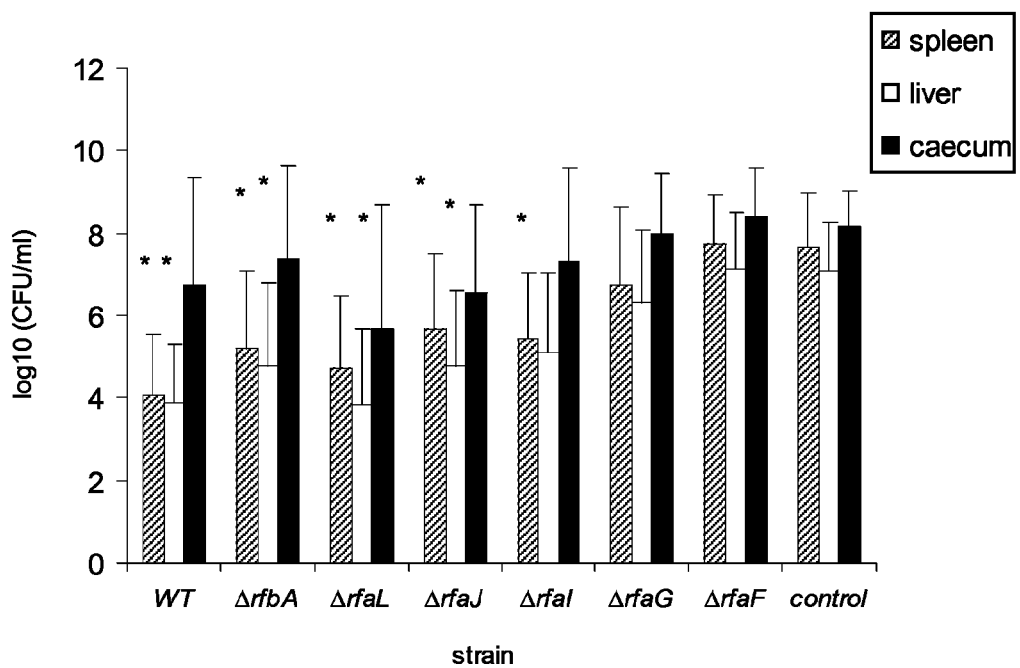
FIG. 5: Recovery of *Salmonella* bacteria from various organs of mice immunized with either *Salmonella Typhimurium*, one of its isogenic LPS mutants or non immunized control animals and subsequently challenged with *Salmonella Typhimurium* strain NCTC12023Nal[20]. The $log_{10}$ value of the ratio of CFU per gram sample and standard deviations are given. An asterisk refers to a significant difference with the control group (P<0.05).
Figure 6A:
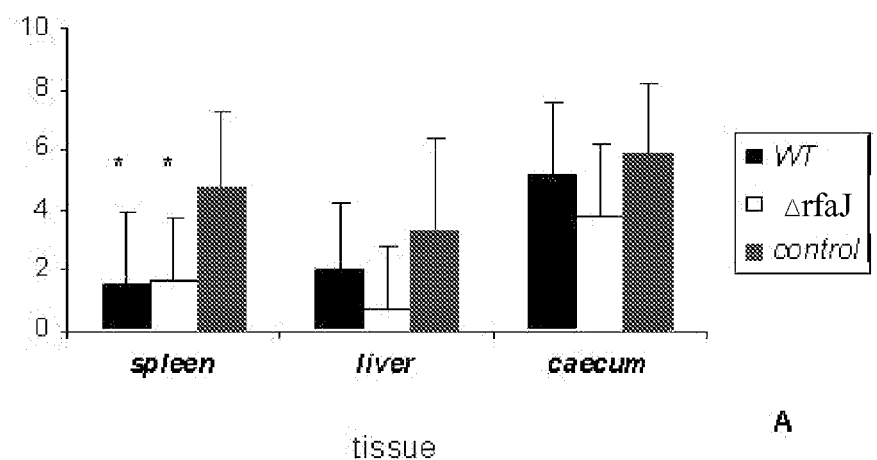
FIG. 6A: Recovery of *Salmonella Heidelberg* bacteria from various organs of BALB/c mice immunized with *Salmonella Typhimurium*, one of its isogenic LPS mutants or uninfected animals subsequently challenged with *Salmonella Heidelberg*. The $log_{10}$ average value of the number of CFU per gram sample is given with its standard deviation. An asterisk refers to a significant difference with the control group (P<0.05).
Figure 6B:
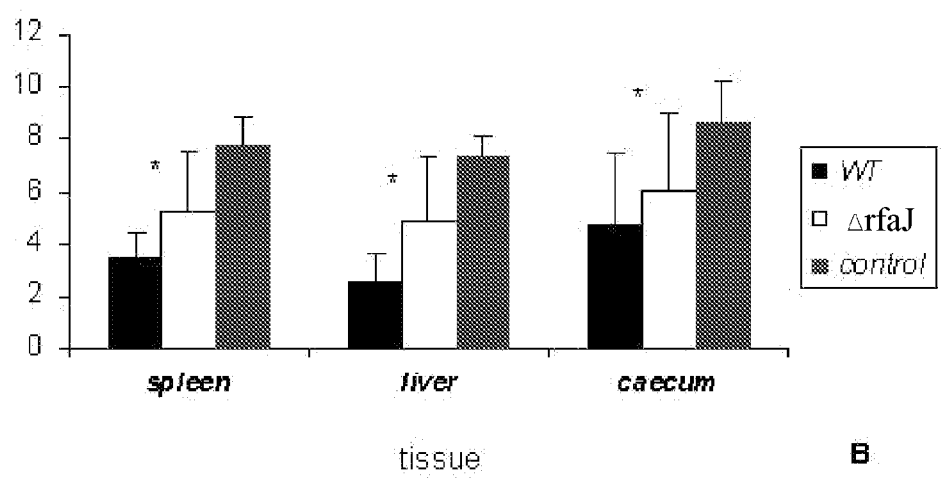
FIG. 6B: Recovery of *Salmonella Enteritidis* bacteria from various organs of BALB/c mice immunized with *Salmonella Typhimurium*, one of its isogenic LPS mutants or uninfected animals subsequently challenged with *Salmonella Enteritidis*. The $log_{10}$ average value of the number of CFU per gram sample is given with its standard deviation. An asterisk refers to a significant difference with the control group (P<0.05).
Figure 7:
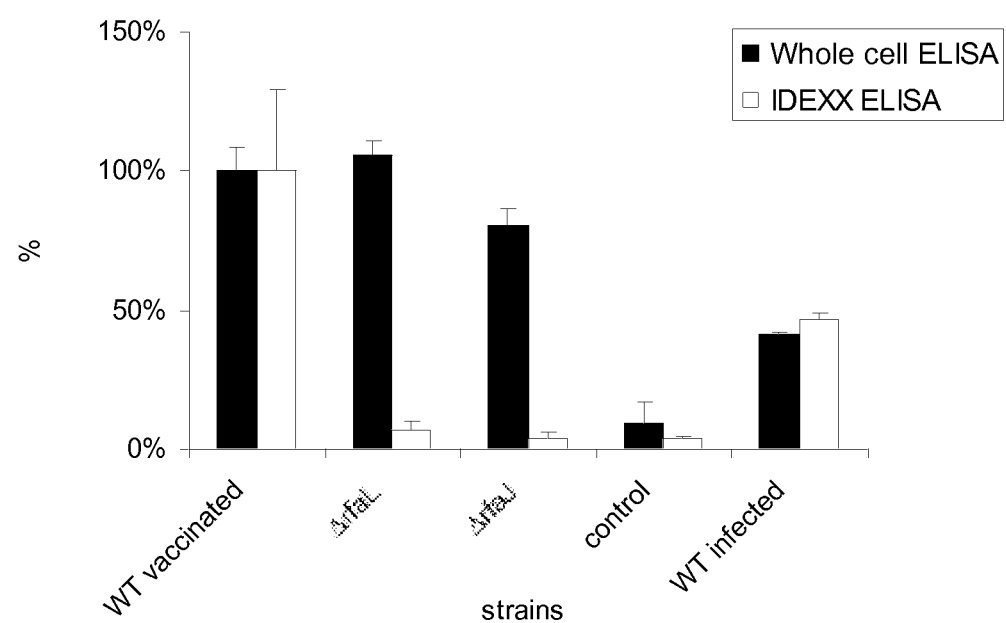
FIG. 7: Serological results of pigs immunized with ΔrfaL, ΔrfaJ or *Salmonella Typhimurium* strain 112910a, control pigs (animals that were not immunized and not infected) and pigs infected with *Salmonella Typhimurium* strain 112910a Nal[20]. Values are represented as a percentage compared to the wild type immunized group.

Further, invasion of *Salmonella Typhimurium* strain 112910a and its isogenic knock-out strains was compared in an IPEC-J2 cell strain, using a gentamicin protection assay. The ΔrfbA, ΔrfaG and ΔrfaF strains showed a statistically significant decrease (P<0.05) in invasion when compared to the 112910a strain, while the ΔrfaL, ΔrfaJ and ΔrfaI strains were not impaired in invasion. Results are summarized in FIG. 4.

2. Deletion of rfaI, rfaG, rfaF Genes but not rfaL and rfaJ Severely Affects the Protective Capacity of *Salmonella Typhimurium* Strain 112910a in BALB/c Mice 2.1. To examine the effect of the LPS deletion on the protective capacity of a live *Salmonella Typhimurium* strain, BALB\c mice were intragastrically vaccinated with either the wild type strain (+ control), the rfaJ mutant strain, the rfbA mutant strain and phosphate buffered saline (PBS; – control). Four weeks after vaccination, these mice were orally challenged with the highly virulent *Salmonella Typhimurium* strain NCTC 12023. In the group of mice sham-vaccinated with PBS, all mice died from systemic salmonellosis within 10 days after inoculation, showing high numbers of bacteria in all internal organs. In the groups of mice vaccinated with either the wild type strain (+ control), the rfaJ mutant strain and the rfbA mutant strain, the majority of mice were alive 10 days after inoculation and all surviving mice were in good clinical condition. These results are shown in FIG. 2.

The results of the quantitative bacteriological examination of the internal organs are shown in FIG. 3.

These results confirm that the LPS deletion does not attenuate the clinical protective capacities of the parental strain in a mouse model.

2.2. Oral immunization of mice with *Salmonella Typhimurium* strain 112910a, ΔrfbA, ΔrfaL or ΔrfaJ strains induced a significant (P<0.05) protection against subsequent challenge with NCTC12023Nal[20] in both spleen and liver compared to non immunized control animals. Bacterial counts (wild type, ΔrfbA, ΔrfaL and ΔrfaJ) in caecum samples showed a non significant (P>0.05) reduction of the numbers of *Salmonella Typhimurium* compared with control animals. Deletion of rfaI, rfaG and rfaF genes but not rfbA, rfaL and rfaJ genes thus significantly (P<0.05) reduced protection against challenge with *Salmonella Typhimurium* strain NCTC12023Nal[20]. None of the animals immunized with ΔrfbA, ΔrfaG or ΔrfaF died as a result of vaccination, whereas eight mice vaccinated with either strain 112910a (n=3), ΔrfaL (n=2), ΔrfaJ (n=2) or ΔrfaI (n=1) died as a consequence of vaccination. After challenge, >60% of the unvaccinated animals or mice vaccinated with either ΔrfaG or ΔrfaF died opposed to <40% of mice vaccinated with wild type, ΔrfaL or ΔrfaJ. Results are illustrated in FIG. 5.

3. Immunization with the Δrfaj Strain does not Confer Enhanced Cross-Protection Against Subsequent Challenge with Serovars *Heidelberg* and *Enteritidis* in BALB/C Mice In this experiment we determined to which extent the ΔrfaJ strain and *Salmonella Typhimurium* strain 112910a were able to confer cross-protection against *Salmonella Heidelberg* or *Salmonella Enteritidis*. Both strains were equally able to induce a significant (P<0.05) reduction of *Salmonella Heidelberg* in the spleen compared to control animals. In liver and caecum both strains induced a noticeable, but non significant (P>0.05) reduction of *Salmonella Heidelberg* compared to control animals.

Recovery of *Salmonella Enteritidis* was not significantly different (P<0.05) in spleen, liver and caecum between animals immunized with *Salmonella Typhimurium* strain 112910a and mice immunized with ΔrfaJ. Results are shown in FIGS. 6A and 6B.

4. Immunological Responses in Pigs 4.1. From the in vivo experiments in pigs with a double intramuscular injection of the formalin inactivated rfaJ and rfbA mutant strain, supplemented with Freund's incomplete adjuvant, it has been found that said mutants elicit a humoral immune response that is comparable to the immune response elicited by a double intramuscular injection of the isogenic formalin inactivated wild type *Salmonella Typhimurium* strain supplemented with Freund's incomplete adjuvant using an in-house whole cell ELISA (Table 1). These experiments prove that the deletion of these genes does not impair the production of *Salmonella*-specific antibodies.

TABLE 1

Percentage OD that was obtained using different commercial ELISA's used in official European monitoring programs and an in house whole-cell ELISA for serum obtained from piglets vaccinated with the wild type strain (+control), the rfaJ mutant strain, the rfbA mutant strain and phosphate buffered saline (PBS; –control).

| Elisa | +control | rfaJ mutant | rfbA mutant | −control |
|---|---|---|---|---|
| Whole cell ELISA | 1.1 ± 0.03 | 1.1 ± 0.08 | 1.1 ± 0.07 | 0.1 ± 0.02 |
| Idexx Herdcheck (% OD) | 23.0 ± 13.0 | −1.8 ± 0.6 | 5.1 ± 1.5 | −2.4 ± 0.3 |
| LDL Salmotype (% OD) | 53.7 ± 16.7 | 14.2 ± 11.5 | 63.0 ± 8.7 | 3.0 ± 6.5 |

It was an object to develop a vaccine that would induce a good immune response, and that is serologically distinguishable from animals infected with *Salmonella*. It was therefore further assessed whether the humoral immune response elicited by the double intramuscular injection of formalin inactivated rfaJ and rfbA mutant strains supplemented with Freund's incomplete adjuvant are serologically distinguishable from animals infected with *Salmonella*. For both commercially available ELISA's, the OD values of the sera obtained from pigs after double intramuscular injection with either formalin inactivated rfaJ mutants supplemented with Freund's incomplete adjuvant or sterile PBS were not statistically different (Table 1).

4.2. IDEXX ELISA: No significant seroconversion (P>0.05) was noticed in pigs immunized with inactivated ΔrfaJ or ΔrfaL strains and in control animals (non immunized and non infected animals). Conversely, marked seroconversion occurred in animals immunized or orally infected with the inactivated *Salmonella Typhimurium* strain 112910a. Statistical analysis showed a significant difference (P<0.05) between the antibody response against *Salmonella Typhimurium* LPS in pigs infected with *Salmonella Typhimurium* 112910a and control animals. Results are shown in FIG. 7. Results also illustrate a clear differentiation between sera from piglets immunized with the ΔrfaJ strain or ΔrfaL strain and sera of pigs infected with their isogenic wild type strain.

Whole-cell ELISA: Significant anti-*Salmonella*-antibody titers were detected in the serum of all immunized and infected animals. No significant distinction (P>0.05) regarding *Salmonella*-specific antibody responses could be made between animals that were immunized with the inactivated 112910a strain and those immunized with the inactivated ΔrfaJ and ΔrfaL strains. Results are shown in FIG. 7.

Example 2

Transmission Study with RfaJ Marker Strain of a Commercial *Salmonella Typhimurium* Vaccine for Use in Pigs

1. Methods and Materials 1.1 Bacterial Strains

The Salmoporc® *Salmonella Typhimurium* vaccine strain is used as the wild type background to construct an isogenic LPS knock-out mutant: in the rfaJ gene as described before. Briefly, the gene of interest is first substituted by a PCR adjusted antibiotic resistance cassette (kanamycin) using the helper plasmid pKD46. This plasmid encodes the phage λ Red system, which promotes recombination between the native gene and the PCR adjusted antibiotic resistance cassette. Recombinant clones are selected by plating on Luria-Bertani agar (LB; Sigma Aldrich Chemie Gmbh, Steinheim, Germany) containing 100 μg/ml kanamycin. The substitution is confirmed by PCR. In the last step, the antibiotic resistance cassettes are eliminated using the helper plasmid pcp20. The targeted genes are completely deleted from the start codon through the stop codon, as confirmed by sequencing. *Salmonella* challenge strain is the spontaneous nalidixic acid resistant *Salmonella Typhimurium* strain $112910a^{nal20}$.

1.2 ELISA Procedures

A commercially available enzyme-linked immunosorbent assay (ELISA) (HerdChek *Salmonella*; IDEXX Laboratories, Schiphol-Rijk, Noord-Holland, The Netherlands) for the detection of porcine antibodies against the LPS of *Salmonella* is used as a reference according to the manufacturer's instructions. Coating antigens in this ELISA include LPS of serogroups B, C1 and D (O-antigens 1, 4, 5, 6, 7 and 12). Besides, an in-house *Salmonella Typhimurium* strain 112910a whole cell ELISA, to detect porcine anti *Salmonella Typhimurium* antibodies, is prepared as described before.

1.3 Testing of the Protective and Marker Capacities of the New Markervaccine

The protective and marker capacities of the new marker vaccine strain is tested in a porcine seeder model. Three-week-old bacteriologically and serologically *Salmonella* negative piglets (commercial closed line based on Landrace) are used. Piglets are randomly allocated in one experimental group (n=2×8), one positive control group (n=2×8) and one negative control group (n=1×8) One day and 22 days after their arrival at the facility, the experimental group is orally vaccinated with the new marker vaccine strain according to the guidelines of the manufacturer for the original Salmoporc® vaccine. The negative and positive control group is sham-vaccinated with PBS. Two weeks after the last vaccination, two piglets per group of eight animals of the positive control group and the experimental group is orally inoculated with approximately $2\times10^7$ CFU/ml of a stationary phase culture of *Salmonella Typhimurium* strain $112910aNal^{20}$ in 2 ml Hank's buffered salt solution (HBSS; Gibco Life Technologies, Paisley, Scotland) and is housed separately during 24 hours; the negative control group (n=3) is sham-inoculated with 2 ml HBSS. Twenty-four hours after inoculation these seeder animals are placed back in their original group. The clinical condition of the pigs is monitored daily. Six weeks after oral inoculation, pigs are humanely euthanized and blood and tissue samples from various organs (tonsils, ileum, caecum, and ileocaecal lymph nodes) is collected. Blood is also collected from all piglets on a weekly basis throughout the entire experiment and fresh faecal samples is collected two times per week. All sera samples are examined for the presence of anti *Salmonella Typhimurium* antibodies using the Herdchek ELISA and the in-house *Salmonella Typhimurium* strain 112910a whole cell ELISA, prepared as described previously. Tissue and faecal samples are examined quantitatively for the presence of *Salmonella*. Samples are weighed and 10% (w/v) suspensions are made in buffered peptone water (BPW; Oxoid, Basingstoke, UK) after which the material is homogenized with a stomacher. The homogenized samples are examined for the presence of *Salmonella* by plating 10-fold dilutions on BGA supplemented with nalidixic acid ($BGA^{NAL}$). If negative at direct plating, the samples are pre-enriched overnight in BPW at 37° C., enriched overnight at 37° C. in tetrathionate broth and then plated on $BGA^{NAL}$. Samples that are negative after direct plating but positive after enrichment are presumed to contain 60 CFU per gram tissue (detection limit for direct plating). Samples that remain negative after enrichment are presumed to contain 0 CFU per gram tissue.

2. Rationale

The current experimental setup allows to quantify the protective capacity of the vaccination in the inoculated pigs (colonization and shedding) and to determine whether vaccination can influence the spreading of *Salmonella* between piglets. In addition, by analysing the blood samples for antibodies, the humoral response after vaccination and after challenge is followed up using both the LPS ELISA and the in-house whole-cell ELISA. This results in the evaluation of the newly developed vaccine strain as a marker vaccine in pigs.

REFERENCES

Barth, S., Bauerfeind, R., 2005. Virulence plasmids of *Salmonella enterica*: incidence and properties. Berl. Munch. Tierarztl. Wochenschr. 118, 8-23.

Bauerfeind R, Barth S, Weiss R, Baljer G. Prevalence of the *Salmonella* plasmid virulence gene "spvD" in *Salmonella* strains from animals. Dtsch Tierarztl Wochenschr. 2001 June; 108(6):243-5.

Hitchcock P J, Leive L, Makela P H, Rietschel E T, Strittmatter W, Morrison D C. Lipopolysaccharide nomenclature: past, present, and future. J Bacteriol 1986 June; 166(3): 699-705.

Namimatsu T, Asai T, Osumi T, Imai Y, Sato S. 2006 Prevalence of the virulence plasmid in *Salmonella Typhimurium* isolates from pigs. J Vet Med. Sci. 68:187-8.

Rychlik I, Gregorova D, Hradecka H. 2006 Distribution and function of plasmids in *Salmonella enterica*. Vet Microbiol. 112:1-10.

Boyen F, Pasmans F, Donne E, Van Immerseel F, Adriaensen C, Hernalsteens J P, Ducatelle R, Haesebrouck F. 2006a. Role of SPI-1 in the interactions of *Salmonella Typhimurium* with porcine macrophages. Vet Microbiol. 113: 35-44.

Boyen F, Pasmans F, Van Immerseel F, Morgan E, Adriaensen C, Hernalsteens J P, et al. *Salmonella Typhimurium* SPI-1 genes promote intestinal but not tonsillar colonization in pigs. Microbes Infect. 2006b November-December; 8(14-15):2899-907.

Boyen F, Haesebrouck F, Maes D, Van Immerseel F, Ducatelle R, Pasmans F. 2008. Non-typhoidal *Salmonella* infections in pigs: a closer look at epidemiology, pathogenesis and control. Vet Microbiol. 130(1-2):1-19.

Boyen F, Pasmans F, Van Immerseel F, Donné E, Morgan E, Ducatelle R, Haesebrouck F. 2009. Porcine in vitro and in vivo models to assess the virulence of *Salmonella enterica* serovar *Typhimurium* for pigs. Lab Anim. 43(1):46-52.

EFSA, Opinion of the Scientific Panel on Biological Hazards on the request from the Commission related to "Risk assessment and mitigation options of *Salmonella* in pig production", EFSA J. 341 (2006), pp. 1-131.

Farzan A, Friendship R M, Dewey C E. Evaluation of enzyme-linked immunosorbent assay (ELISA) tests and culture for determining *Salmonella* status of a pig herd. Epidemiol Infect 2007 February; 135(2):238-44.

Nichols E F, Madera L, Hancock R E W. Immunomodulators as adjuvants for vaccines and antimicrobial therapy. Ann. N.Y. Acad. Sci. (2010) 1-16

Nikaido, H., 1996. Outer membrane. In: Neidhardt, F. C. Editor, 1996. *Escherichia* and *Salmonella*: Cellular and Molecular Biology (2nd ed.), ASM Press, Washington D.C., page 30.

Datsenko K A, Wanner B L. One-step inactivation of chromosomal genes in *Escherichia coli* K-12 using PCR products. Proc Natl Acad Sci USA. 2000 Jun. 6; 97(12):6640-5.

E. Donné, F. Pasmans, F. Boyen, F. Van Immerseel, C. Adriaensen, J. P. Hernalsteens, R. Ducatelle and F. Haesebrouck, Survival of *Salmonella* serovar *Typhimurium* inside porcine monocytes is associated with complement binding and suppression of the production of reactive oxygen species, Vet. Microbiol. 107 (2005), pp. 205-214.

Hensel M, Shea J E, Gleeson C, Jones M D, Dalton E, Holden D W. Simultaneous identification of bacterial virulence genes by negative selection. Science 1995 Jul. 21; 269 (5222):400-3.

The invention claimed is:

1. A method of using a *Salmonella enterica* mutant strain in the treatment or prevention of *Salmonella* infection, comprising:
   providing a *Salmonella enterica* mutant strain having a deletion of the rfaL and/or rfaJ gene; and
   immunizing a poultry, cattle, swine and/or pig with an immunizing amount of said strain.

2. A method for treating or preventing a *Salmonella* infection comprising administering an immunizing amount of a *Salmonella enterica* mutant strain having a deletion of the rfaL and/or rfaJ gene to a swine or pig.

3. A method for immunizing a pig with a serological marker vaccine against *Salmonella* comprising:

provi ding a vaccine comprising a *Salmonella enterica* mutant strain having a deletion of the rfaL and/or rfaJ gene;

immunizing said pig with an immunizing amount of said *Salmonella enterica* mutant strain; thereby inducing an immune response that is serologically distinguishable from an infection with a wild-type *Salmonella* strain.

4. The method of claim 1, wherein said *Salmonella enterica* mutant strain is selected from the group consisting of *Salmonella* ser. *Typhimurium* (*S. Typhimurium*), *Salmonella* ser. *Choleraesuis* (*S. Choleraesuis*), *Salmonella* ser. *Derby* (*S. Derby*), *Salmonella* ser. *Infantis* (*S. Infantis*), *Salmonella* ser. *Bredeney* (*S. Bredeney*), *Salmonella* ser. *Rissen* (*S. Rissen*), and *Salmonella* ser. *Anatum* (*S. Anatum*).

5. The method of claim 1, wherein the *Salmonella enterica* mutant strain is *Salmonella Typhimurium*.

6. The method of claim 2 wherein the *Salmonella enterica* mutant strain further comprises one or more mutations in addition to said deletion.

7. The method of claim 3 wherein the *Salmonella enterica* mutant strain further comprises one or more mutations in addition to said deletion.

8. The method of claim 1, wherein the *Salmonella enterica* mutant strain is obtained by deleting the rfaL and/or rfaJ genes in the *Salmonella Typhimurium* strain deposited under accession number LMG P-25625.

9. The method of claim 2, wherein the *Salmonella enterica* mutant strain is obtained by deleting the rfaL and/or rfaJ genes in the *Salmonella Typhimurium* strain deposited under accession number LMG P-25625.

10. The method of claim 3, wherein the *Salmonella enterica* mutant strain is obtained by deleting the rfaL and/or rfaJ genes in the *Salmonella Typhimurium* strain deposited under accession number LMG P-25625.

11. The method of claim 1, wherein the *Salmonella enterica* mutant strain is attenuated or inactivated.

12. The method of claim 2, wherein the *Salmonella enterica* mutant strain is attenuated or inactivated.

13. The method of claim 3, wherein the *Salmonella enterica* mutant strain is attenuated or inactivated.

14. The method of claim 1, wherein the *Salmonella enterica* mutant strain is provided together with a pharmaceutically acceptable carrier or diluent.

15. The method of claim 2, wherein the *Salmonella enterica* mutant strain is administered together with a pharmaceutically acceptable carrier or diluent.

16. The method of claim 3, wherein the vaccine further comprises a pharmaceutically acceptable carrier or diluent, and optionally an adjuvant.

* * * * *

SEQUENCE LISTING

```
<160> NUMBER OF SEQ ID NOS: 16

<210> SEQ ID NO 1
<211> LENGTH: 1011
<212> TYPE: DNA
<213> ORGANISM: Salmonella enterica

<400> SEQUENCE: 1
ttatttgtgg aaaagtttac gataaagata tgcgcttcca gccagaaggc ctttaaaata      60
atgaccttgc acgagaagat gtttatatcg cttcttaaat tcgactatgg tacgcgcatc     120
ttttgcggga aaatctttcc agggcgagtt cagtcgtgca tttttataat agataactga     180
aggataattt gcccaggcat gccatggttt tgtagcgccc gtataatgaa ttaaaatagt     240
attatcatta attatattgc tatatttttt atgtgactta tctttcaact cacttttaat     300
agtataaata gtattatacg gtcgcggtag aaaaatgact ttatcctgta ggagaatatt     360
caaaacatcc tgatcgggat atttaaaaga gtcagcctct ttacctgcca aaagtaaaaa     420 tgccttttg gttaaggcat tctctttcca taatttcagg ttaacaaaaa ccacgccgga     480
gttaaaataa ccaccttgta aattaaaagc gcttaatctc tcatttacct tattctggat     540
ggaatcaaca tcttttacga ccgcagcgat cttctctgtc agatcaagct gtaaaagatc     600
ttgcaaagat cctttgcata caacatcggc atccaaataa agtaaggtat ttaccttctt     660
gctgagataa tcgaaagcaa ataaacgaaa atacattgct ctcgaccata ctttagtttg     720
aggcaatacc tcaaggcttt ctactttaat aagataaaga gaaattttta tgtgatgctg     780
tacggctaaa cgctctatat attttacaaa acacggggag tatgagtcac aaataatgtg     840
aaaagcgagc gggatattat tgtttaatac aactgaagcg attgataccc ccacaccatc     900
aagatagttt tcatcaacgc cataagaaat gtttaatacg ttatcatcat tattattact     960
ttcatcaaaa actttatatt cagctatttc tatctcagga aatgaatcca t            1011

<210> SEQ ID NO 2
<211> LENGTH: 1215
<212> TYPE: DNA
<213> ORGANISM: Salmonella enterica

<400> SEQUENCE: 2
atgctaacca catcattaac gttaaataaa gagaaatgga agccgatctg gaataaagcg      60 ctggttttc tttttgttgc cacgtatttt ctggatggta ttacgcgtta taacatttg     120 ataatcatac ttatggttat caccgcgatt tatcaggtct cacgctcacc gaaaagtttc     180
cccctctttt tcaaaaatag cgtattttat agcgtagcag tattatcatt aatccttgtt     240
```

```
tattccatac tcatatcgcc agatatgaaa gaaagtttca aggaatttga aaatacggta        300
ctggagggct tcttattata tactttatta attcccgtac tattaaaaga tgaaacaaaa        360
gaaacggttg cgaaaatagt acttttctcc tttttaacaa gtttaggact tcgctgcctt        420
gcagagagta ttctgtatat cgaggactat aataaaggga ttatgccatt cataagctat        480
gcgcatcgac atatgtccga ttccatggtt ttcttatttc cagcattatt gaatatttgg        540
ctgtttagaa aaaatgcaat taagttggtt ttttggtgc ttagcgccat ctaccttttc         600
tttatcctgg gaaccctatc gcgaggggca tggttggcgg tgcttatagt aggtgttctg        660
tgggcaatac tgaaccgcca atggaagtta ataggagttg gtgccatttt attagccatt        720
atcggcgctt tggttatcac tcaacataat aacaaaccag acccagaaca tttactgtat        780
aaattacagc agacagatag ctcatatcgt tatactaacg gaacccaggg caccgcgtgg        840
atactgattc aggaaaaccc gatcaagggc tacggctatg gtaatgatgt gtatgatggt        900
gtttataata aacgcgttgt cgattatcca acgtggacct ttaaagaatc tatcggtccg        960
cataatacca ttctgtacat ctggtttagt gcaggcatat tgggtctggc gagcctggtc       1020
tatttatatg gcgctatcat cagggaaaca gccagctcta ccctcaggaa agtagagata       1080 agccctaca atgctcatct cttgctattt ttatctttcg tcggttttta tatcgttcgt        1140
ggcaattttg aacaggtcga tattgctcaa attggtatca ttaccggttt tctgctggcg       1200
ctaagaaata gataa                                                        1215
```

```
<210> SEQ ID NO 3
<211> LENGTH: 71
<212> TYPE: DNA
<213> ORGANISM: Artificial
<220> FEATURE:
<223> OTHER INFORMATION: Primer Sequences

<400> SEQUENCE: 3
atagcctact ttaaacgtaa acttcttgaa taaaacccat aggtgatgta tgtgtaggct         60
ggagctgctt c                                                             71

<210> SEQ ID NO 4
<211> LENGTH: 70
<212> TYPE: DNA
<213> ORGANISM: Artificial
<220> FEATURE:
<223> OTHER INFORMATION: Primer sequences

<400> SEQUENCE: 4
agtttttaat ctttttttca ataatcataa tggagattta gggaggggaa catatgaata         60
tcctccttag                                                               70

<210> SEQ ID NO 5
<211> LENGTH: 71
<212> TYPE: DNA
<213> ORGANISM: Artificial
<220> FEATURE:
<223> OTHER INFORMATION: Primer Sequences

<400> SEQUENCE: 5
taataaattt aaatgcccat caggcatttt tctatgaatg agaaatggaa tgtgtaggct         60
ggagctgctt c                                                             71

<210> SEQ ID NO 6
```

```
<211> LENGTH: 70
<212> TYPE: DNA
<213> ORGANISM: Artificial
<220> FEATURE:
<223> OTHER INFORMATION: Primer Sequences

<400> SEQUENCE: 6
ggctctaaga tcaagacatc tggtattgct gttttaatca caatcatcac catatgaata      60
tcctccttag                                                            70

<210> SEQ ID NO 7
<211> LENGTH: 66
<212> TYPE: DNA
<213> ORGANISM: Artificial
<220> FEATURE:
<223> OTHER INFORMATION: Primer Sequences

<400> SEQUENCE: 7
cattaaagag actctgtctc atcccaaacc tattgtggag aaaagtgtgt aggctggagc      60
tgcttc                                                                66

<210> SEQ ID NO 8
<211> LENGTH: 55
<212> TYPE: DNA
<213> ORGANISM: Artificial
<220> FEATURE:
<223> OTHER INFORMATION: Primer Sequences

<400> SEQUENCE: 8
ttgagtcctg atgatggaaa acgcgctgat accgtcatat gaatatcctc cttag          55

<210> SEQ ID NO 9
<211> LENGTH: 71
<212> TYPE: DNA
<213> ORGANISM: Artificial
<220> FEATURE:
<223> OTHER INFORMATION: Primer Sequences

<400> SEQUENCE: 9
tttaaaaatt ttaataatgc aatattctcg aaattacaaa agtgatcact tgtgtaggct      60
ggagctgctt c                                                          71

<210> SEQ ID NO 10
<211> LENGTH: 70
<212> TYPE: DNA
<213> ORGANISM: Artificial
<220> FEATURE:
<223> OTHER INFORMATION: Primer Sequences

<400> SEQUENCE: 10
ttcagctatt tctatctcag gaaatgaatc cattacatca cctatgggtt catatgaata      60
tcctccttag                                                            70

<210> SEQ ID NO 11
<211> LENGTH: 71
<212> TYPE: DNA
<213> ORGANISM: Artificial
<220> FEATURE:
<223> OTHER INFORMATION: Primer Sequences

<400> SEQUENCE: 11
gaaaaaatgc tgccgcatga ggcacgcacc atagatttgg acagcctgct tgtgtaggct      60
ggagctgctt c                                                          71
```

```
<210> SEQ ID NO 12
<211> LENGTH: 70
<212> TYPE: DNA
<213> ORGANISM: Artificial
<220> FEATURE:
<223> OTHER INFORMATION: Primer Sequences

<400> SEQUENCE: 12
cctcaaaagc atctttaccg cgccatagtg tggttaacgg cgctttcagc catatgaata    60
tcctccttag                                                           70

<210> SEQ ID NO 13
<211> LENGTH: 71
<212> TYPE: DNA
<213> ORGANISM: Artificial
<220> FEATURE:
<223> OTHER INFORMATION: Primer Sequences

<400> SEQUENCE: 13
gccgaaggcg tcacggagta tatggcctgg ctgaaccgcg acgcgtaagt tgtgtaggct    60
ggagctgctt c                                                         71

<210> SEQ ID NO 14
<211> LENGTH: 70
<212> TYPE: DNA
<213> ORGANISM: Artificial
<220> FEATURE:
<223> OTHER INFORMATION: Primer Sequences

<400> SEQUENCE: 14
ggtatgtaat acgtcgccca tcgatgatgt tttaacgatc aaaacccgca catatgaata    60
tcctccttag                                                           70

<210> SEQ ID NO 15
<211> LENGTH: 71
<212> TYPE: DNA
<213> ORGANISM: Artificial
<220> FEATURE:
<223> OTHER INFORMATION: Primer Sequences

<400> SEQUENCE: 15
cagcgggttc tggaagagct tcattcgctg ttgtcggaag agggcgttta tgtgtaggct    60
ggagctgctt c                                                         71

<210> SEQ ID NO 16
<211> LENGTH: 70
<212> TYPE: DNA
<213> ORGANISM: Artificial
<220> FEATURE:
<223> OTHER INFORMATION: Primer Sequences

<400> SEQUENCE: 16
gtggttagca tcttttctcc acaataggtt tgggatgaga cagagtctct catatgaata    60
tcctccttag                                                           70
```